(12) United States Patent
Park et al.

(10) Patent No.: US 9,933,424 B2
(45) Date of Patent: Apr. 3, 2018

(54) HUMAN RESISTIN RECEPTOR AND USE THEREOF

(75) Inventors: Young Bae Park, Seoul (KR); Hyo Soo Kim, Seoul (KR); Yoo Wook Kwon, Seoul (KR); Sahmin Lee, Seoul (KR); Hyun Chae Lee, Seoul (KR); Young Jin Cho, Seoul (KR); Sang Eun Lee, Seoul (KR); Jun Ho Chung, Seoul (KR)

(73) Assignee: Seoul National University Hospital, Seoul (KR)

( * ) Notice: Subject to any disclaimer, the term of this patent is extended or adjusted under 35 U.S.C. 154(b) by 0 days.

(21) Appl. No.: 14/237,518

(22) PCT Filed: Aug. 7, 2012

(86) PCT No.: PCT/KR2012/006269
§ 371 (c)(1),
(2), (4) Date: Feb. 6, 2014

(87) PCT Pub. No.: WO2013/022262
PCT Pub. Date: Feb. 14, 2013

(65) Prior Publication Data
US 2014/0171489 A1 Jun. 19, 2014

(30) Foreign Application Priority Data

Aug. 8, 2011 (KR) .......... 10-2011-0078692
Aug. 7, 2012 (KR) .......... 10-2012-0086475

(51) Int. Cl.
*G01N 33/53* (2006.01)
*G01N 33/564* (2006.01)
*G01N 33/68* (2006.01)

(52) U.S. Cl.
CPC ....... *G01N 33/564* (2013.01); *G01N 33/6863* (2013.01); *G01N 2333/715* (2013.01)

(58) Field of Classification Search
None
See application file for complete search history.

(56) References Cited

FOREIGN PATENT DOCUMENTS

| KR | 10-2008-0045953 A | 5/2008 |
|----|-------------------|--------|
| WO | WO 2004-034062 A2 | 4/2004 |
| WO | WO 2010-113148 A1 | 10/2010 |

OTHER PUBLICATIONS

B.S. Youn et al; Plasma resistin concentrations measured by . . . ; J. Clin Endocrinol Metab.; Jan. 2004; vol. 89, No. 1, pp. 150-156.
S. Pang et al; Role of resistin in inflammation and inflammation-related . . . ; Cell Mol Immunol.; Feb. 2006; vol. 3, No. 1.
International Search Report dated Feb. 19, 2013.

*Primary Examiner* — Michael Pak
(74) *Attorney, Agent, or Firm* — Lucas & Mercanti, LLP

(57) ABSTRACT

The present invention concerns a human resistin receptor. More particularly, the present invention provides a method for screening a receptor of human resistin protein, a method for preventing or treating an inflammatory disease and arteriosclerosis using an expression- or activity-regulator for a human resistin receptor, and a pharmaceutical composition including an expression- or activity-regulator for the human resistin receptor. The method for screening a human resistin protein receptor according to the present invention enables separation of a receptor which directly binds to resistin from human monocyte, reveals a mechanism of signal transduction of the resistin receptor, and therefore, is expected to contribute to regulation of an inflammatory effect of monocyte, molecular detection of causes for vascular inflammation and arteriosclerosis, and developments of prevention and a treating agent for an inflammatory disease and arteriosclerosis.

8 Claims, 26 Drawing Sheets

FIG. 21
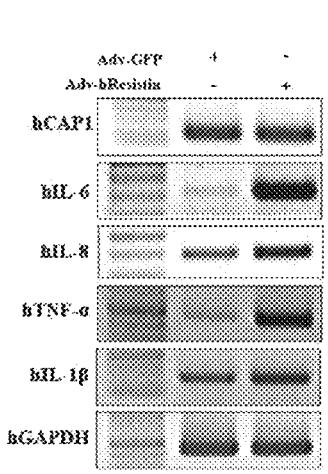
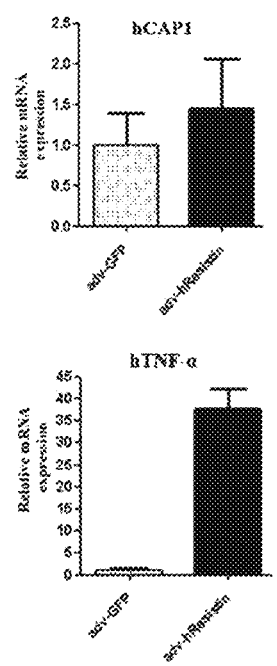
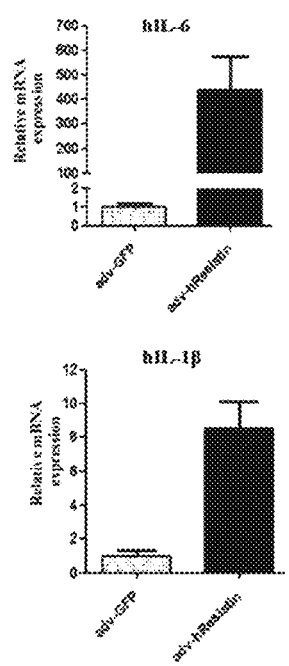
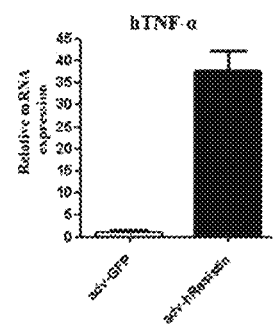
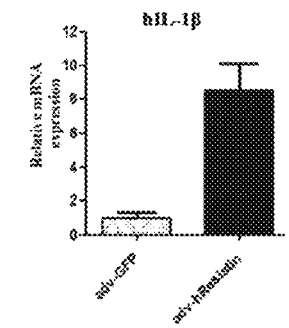
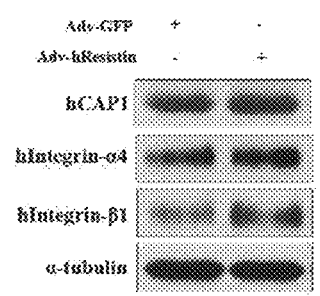
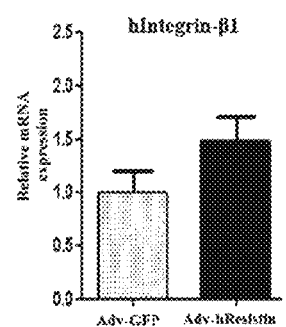

HUMAN RESISTIN RECEPTOR AND USE THEREOF

CROSS-REFERENCE TO RELATED APPLICATIONS

This application is a 371 of PCT/KR2012/006269, filed Aug. 7, 2012, which claims the benefit of Korean Patent Application No. 10-2012-0086475, filed Aug. 7, 2012 and of Korean Patent Application No. 10-2011-0078692, filed Aug. 8, 2011, the contents of each of which are incorporated herein by reference.

STATEMENT REGARDING GOVERNMENT RIGHTS

This study was supported by a grant of the Korea Healthcare technology R&D Project, Ministry of Health and Welfare, Republic of Korea (A062260) and National Research Foundation grant funded by the Korea government (MEST) [2010-0020257].

The present invention was undertaken with the support of Establishment of the Research-driven Hospital through Open Innovation Collaboration: Platform Technologies for Cancer-Inflammatory & Metabolic Disease No. HI14C1277 grant funded by the Korea Health Industry Development Institute funded by the Ministry of Health & Welfare.

TECHNICAL FIELD

The present invention relates to a human resistin receptor, more particularly, to a method for screening a receptor of human resistin protein, a method for preventing or treating an inflammatory disease and arteriosclerosis using an expression- or activity-regulator for the human resistin receptor, and a pharmaceutical composition including an expression- or activity-regulator for the human resistin receptor.

BACKGROUND ART

Resistin is a cytokine which is a firstly-acknowledged mediator which induces an insulin resistance in an obese mouse. The cytokine belongs to the cysteine-rich proteins, is also known as resistin-like molecules (RELMs), and is related to regulation of an inflammatory process. Moreover, murine resistin is known to be related to an obesity-mediated insulin resistance and an occurrence of Type 2 diabetes.

In fact, the protein sequences of rat resistin and human resistin are identical by only about 60%. Rodents resistin is firstly expressed and secreted mainly in mature adipocytes, whereas human resistin is secreted mainly in peripheral blood mononuclear cell (PBMC), such as leukocytes, and macrophage. Although it has been revealed through various researches that the function of resistin is different between humans and rodents, the complete understanding therefor has not been reached yet due to a lack of information on resistin receptor and signal transduction pathway.

Human resistin is believed to be related to a recruitment of other immune cells and secretion of pro-inflammatory factor, and there have been continuous proofs that it is related to an inflammatory disease and arteriosclerosis regardless of the existence of insulin resistance.

A resistin which exists both in rat and human arteriosclerosis lesion is known as an inflammatory marker of arteriosclerosis in human, and also, is known to accelerate arteriosclerosis by activating monocyte. Accordingly, human resistin is believed to be a critical factor which regulates the monocyte leading an arteriosclerosis process.

Large parts of an inflammatory-related mechanism in human resistin seem to be regulated by an activity of nuclear factor kappa B (NF-κB) transcription factor, yet the signal transduction pathway which shows a pro-inflammatory effect of resistin is still unclear, and in addition, a receptor closely related to the resistin has not been confirmed yet.

Accordingly, a discovery of the receptor which directly interacts with human resistin as well as a clear understanding on its signal transduction pathway are required in the art.

DISCLOSURE

Technical Problem

The technical problem to be solved by the present invention is to provide a method for screening a human resistin receptor. In addition, the present invention provides a method for preventing or treating an inflammatory disease and arteriosclerosis by regulating an activity of the human resistin receptor screened by the method, and a pharmaceutical composition including an expression- or activity-regulator for the human resistin receptor.

However, the problem to be solved by the present invention is not limited to those indicated above, and the other problems which are not described herein would be clearly understood by those skilled in the art via the following description.

Technical Solution

One aspect of the present invention, therefore, provides a method for screening a human resistin protein receptor, including: a) a step of preparing a recombinant vector by cloning mFc [mouse fragment crystallizable (Fc) region of immunoglobulin]-human resistin recombinant DNA to an expression vector; b) a step of expressing mFc human resistin fusion protein by transfecting the recombinant vector to a cell strain; c) a step of forming a complex of mFc human resistin fusion protein and human resistin receptor by cultivating the expressed mFc human resistin fusion protein together with cells; d) a step of immunoprecipitating the complex and separating the human resistin receptor from the precipitate; and e) a step of confirming the separated human resistin receptor.

Another aspect of the present invention provides a method for screening a human resistin protein receptor, including: a) a step of preparing a recombinant vector by cloning mFc-human resistin recombinant DNA in which mFc gene binds to N-terminal of human resistin gene to an expression vector; b) a step of expressing mFc human resistin fusion protein by transfecting the recombinant vector to HEK293F cells; c) a step of purifying the expressed mFc human resistin fusion protein; d) a step of forming a complex of mFc human resistin fusion protein and a human resistin receptor by cultivating the purified mFc human resistin fusion protein with THP-1 cells; e) a step of immunoprecipitating the complex to obtain a precipitate using beads specific to mFc; f) a step of separating the human resistin receptor corresponding to a size of 55 kDa from the precipitate; and g) a step of confirming the separated human resistin receptor by mass spectrometry.

Still another aspect of the present invention provides a method for treating or preventing a disease by administering an expression- or activity-regulator for the human resistin protein receptor screened by the method to an individual.

Yet another aspect of the present invention provides a method for screening a treating agent for an inflammatory disease or arteriosclerosis, including a step of screening a material which regulates an expression or activity of the human resistin protein receptor screened by the method, wherein the human resistin protein receptor is adenylyl cyclase-associated protein 1 (CAP1).

Yet still another aspect of the present invention provides a pharmaceutical composition for treating and/or preventing an inflammatory disease or arteriosclerosis, including an expression- or activity-regulator for the human resistin protein receptor screened by the method.

Advantageous Effects

The method for screening a human resistin protein receptor according to the present invention enables separation of a receptor which directly binds to resistin from human monocyte, reveals a mechanism of signal transduction of the resistin receptor, and therefore, is expected to contribute to regulation of an inflammatory effect of monocyte, molecular detection of causes for vascular inflammation and arteriosclerosis, and further, developments of prevention and a treating agent for an inflammatory disease and arteriosclerosis.

DESCRIPTION OF DRAWINGS

FIG. 21 illustrates an increase of expression of inflammatory cytokine in accordance with resistin treatment.

MODES OF THE INVENTION

Figure 1:
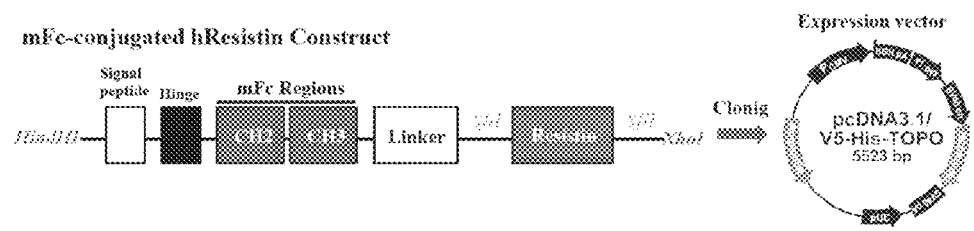
FIG. 1 illustrates a structure of recombinant DNA which encodes mFc-human resistin protein and an expression vector.

The present inventors, via extensive research on the mechanism of human resistin, have surprisingly found that adenylyl cyclase-associated protein 1 (CAP1) protein existing in a cell membrane of human mononuclear leukocyte directly binds to resistin and interacts, and accordingly, have reached to complete the present invention.

The present invention provides a method for screening a human resistin protein receptor including the following steps: a) a step of preparing a recombinant vector by cloning mFc-human resistin recombinant DNA to an expression vector; b) a step of expressing mFc human resistin fusion protein by transfecting the recombinant vector to a cell strain; c) a step of forming a complex of mFc human resistin fusion protein and a human resistin receptor by cultivating the expressed mFc human resistin fusion protein together with cells; d) a step of immuno-precipitating the complex and separating the human resistin receptor from the precipitate; and e) a step of confirming the separated human resistin receptor.

In the mFc-human resistin recombinant DNA in the step a) of the present invention, mFc gene may bind to N-terminal of human resistin gene, and the expression vector may include pcDNA3.1, but the present invention is not limited thereto.

The cell strain in the step b) may include HEK293F cells, but the present invention is not limited thereto.

In addition, the method of the present invention may further include a step of purifying the expressed mFc human resistin fusion protein.

In the step c) of the present invention, the cell may include a human acute monocytic leukemia cell (THP-1), but the present invention is not limited thereto. The step c) may include the cultivation of the mFc human resistin fusion protein together with an anti-mFc-FITC secondary antibody.

In the step d) of the present invention, the immuno-precipitation can be conducted by using beads specific to mFc, and the human resistin receptor may be characterized by being a protein having a size of 55 kDa.

Further, the present invention provides a method for screening a human resistin protein receptor including the following steps: a) a step of preparing a recombinant vector by cloning mFc-human resistin recombinant DNA in which mFc gene is bound to N-terminal of human resistin gene to an expression vector; b) a step of expressing mFc human resistin fusion protein by transfecting the recombinant vector to HEK293F cells; c) a step of purifying the expressed mFc human resistin fusion protein; d) a step of forming a complex of mFc human resistin fusion protein and a human resistin receptor by cultivating the purified mFc human resistin fusion protein together with THP-1 cells; e) a step of immuno-precipitating the complex to obtain a precipitate using beads specific to mFc; f) a step of separating the human resistin receptor corresponding to a size of 55 kDa from the precipitate; and g) a step of confirming the separated human resistin receptor by mass spectrometry.

Furthermore, the present invention provides a pharmaceutical composition for preventing and/or treating an inflammatory disease or arteriosclerosis, including an expression- or activity-regulator for the human resistin protein receptor screened by the method, wherein the human resistin protein receptor includes CAP1 protein.

In addition, the present invention provides a method for preventing and/or treating an inflammatory disease or arteriosclerosis by administering the pharmaceutical composition to an individual.

In the present invention, "individual" is understood to denote a subject which requires a treatment of disease, in particular, mammals such as humans, or non-human primates, mice, rats, dogs, cats, horses, and cattle. Also, in the present invention, a pharmaceutically-effective amount can differ depending on weight, age, sex, health, diet, administration time, administration method, excretion rate, and severity of a disease of a patient, and such a varied range and control thereof should be obvious to those skilled in the art.

A preferred dosage of the pharmaceutical composition of the present invention may differ depending on the condition and weight of a patient, degree of disease, drug form, administration pathway and duration, and can be appropriately selected by those skilled in the art. Nevertheless, the administration can be conducted preferably in an amount of 0.001 to 100 mg/weight kg per day, more preferably in an amount of 0.01 to 30 mg/weight kg per day. The administration may be conducted once a day, or divided into several times.

The pharmaceutical composition of the present invention can be administered to mammals, such as rats, mice, livestock, and humans in various pathways. A method for administration is not particularly limited, and can be, for instance, oral, rectal, or intravenous, intramuscular, subcutaneous, intrauterine intradural, or intra cerbroventricular injection.

The pharmaceutical composition of the present invention can be manufactured in various pharmaceutical formulations, and a form of the formulation is not particularly limited.

The present inventors replicated mFc-human resistin protein to easily find out a complex of resistin protein and a resistin receptor, and believed that the receptor protein can be screened through a screening of complexes to which mFc-human resistin protein binds.

Accordingly, the present inventors prepared mFc-human resistin recombinant DNA, cloned it to an expression vector, and the recombinant vector was transfected to a cell strain to express recombinant DNA, thereby preparing mFc-human resistin recombinant protein. Then, a receptor which binds to the mFc-human resistin protein was confirmed in THP-1 cell extract, and this receptor was revealed to be adenylyl cyclase-associated protein 1 (CAP1) through a mass spectrometry (refer to FIG. 1 to FIG. 4).

Figure 6:
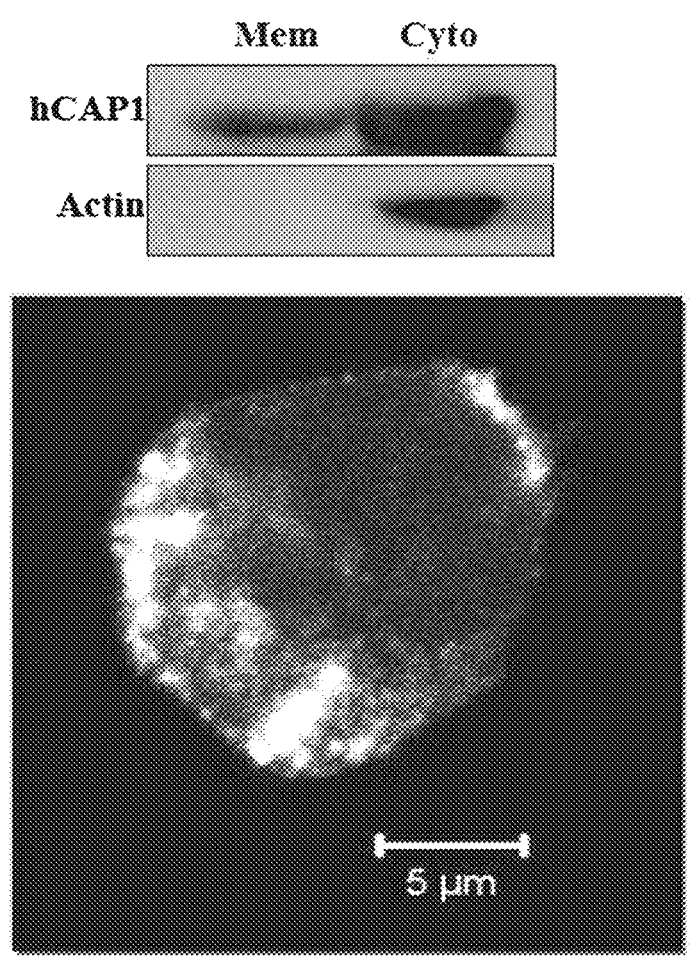
FIG. 6 illustrates results of western blot and immunofluorescence staining which show the position of CAP1 protein in the cell.
Figure 7:
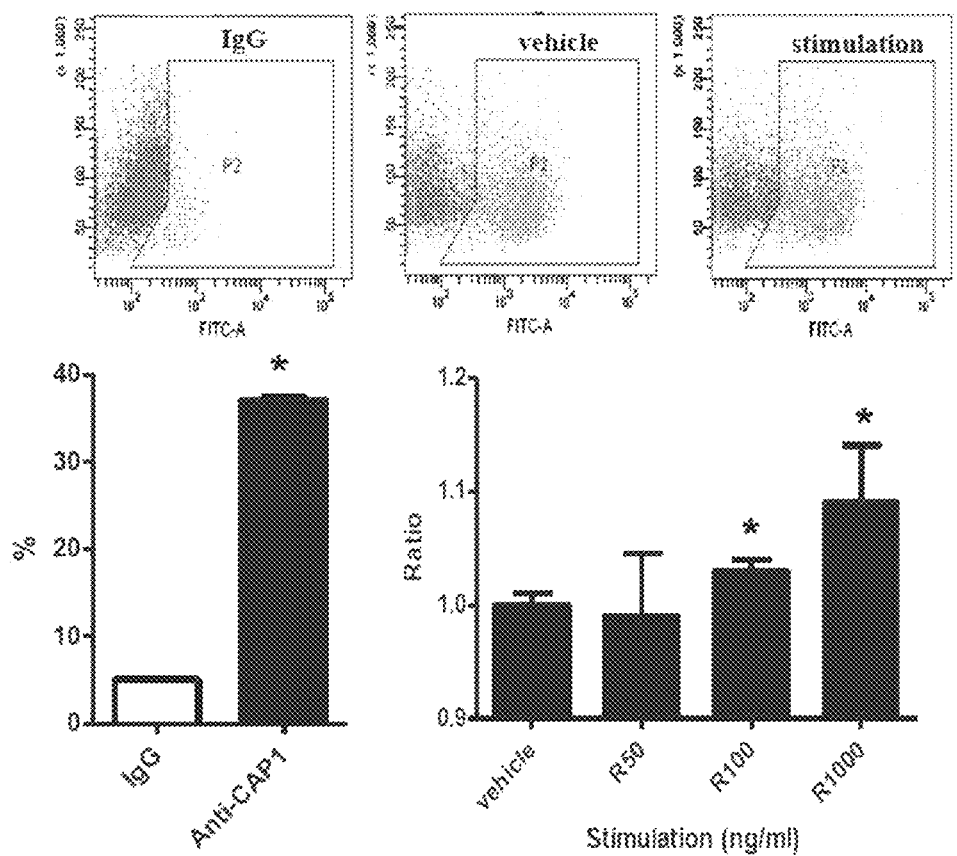
FIG. 7 illustrates results of flow cytometry which classifies THP-1 cells to which a monoclonal antibody of human CAP1 binds.

The present inventors proved, through western blot, immunofluorescence staining, and flow cytometry, that an extracellular human resistin binds to the CAP1 protein screened by the method in monocyte plasma membrane (refer to FIG. 6 and FIG. 7).

Further, the present inventors clearly revealed, through co-immuno-precipitation, far western blotting, and research on receptor's competitive binding, that human resistin and CAP1 directly interact and form a complex (refer to FIG. 8 to FIG. 12).

Figure 13:
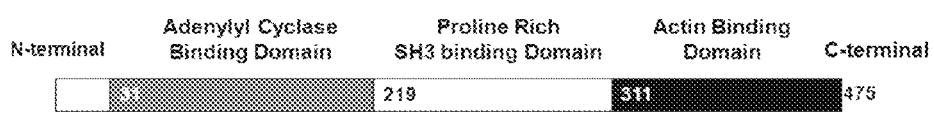
FIG. 13 illustrates a schematic diagram showing three main domains of human CAP1.

In the present invention, CAP1 can be divided into three domains in terms of structural and functional aspects (refer to FIG. 13).

First, a highly-preserved carboxyl-terminal domain binds to actin of a monomer, and is essential to a general cyto-morphology. Second, an amino-terminal domain of CAP1 interacts with adenylyl cyclase in yeast. However, a function of N-terminal in higher eukaryotic cell is not known. NH2-terminal has less identical amino acids than carboxyl-terminal, and it could be understood that the domain related to cell signal may show a difference in contrast to the fact that the function of actin binding domain is preserved according to the research result of protein alignment for an analysis of all reserved portions of CAP. Furthermore, determination as to whether an appearance of CAP1/adenylyl cyclase combination is preserved in humans would be interesting since a structure of adenylyl cyclase structure is not preserved during evolution. Third, a proline-rich domain which exists in the center seems to interact with Src homology 3 (SH3) domain of particular proteins.

On the other hand, CAP1 protein is believed to be an oligomer structure which is a dimer, an amino-terminal domain of CAP1 per se can interact, and a carboxyl-terminal may exist in a form of parallel- or antiparallel-dimer. As a poly-proline domain necessarily exists in the center of the protein, the poly-proline SH3 interaction domain freely binds to a target protein in the both models.

The present inventors used homology modeling in order to reveal a structure of SH3 binding domain of CAP1. The homology modeling is the most simple and trustworthy upon predicting a molecular structure. A foundation of this modeling is based on the fact that proteins having similar sequence tend to be fold in a similar structure. Generally, 30% of the sequence should be identical in order to make a useful model, and the proteins having 25% of identical sequence is fold in a similar structure.

The present inventors predicted poly-proline SH3 binding domain of CAP1 by using Discovery Studio 2.5 (Accelrys Inc.) (refer to FIG. 15).

Further, the present inventors have tried to reveal a signal transduction pathway of resistin, and as a result, confirmed a decrease of cAMP concentration, activity of protein kinase A (PKA) and nuclear factor kappa B (NF-κB), and expression of inflammatory cytokine.

The result is based on the fact that a structure of resistin is important in showing a satisfactory reaction in regulating a macrophage function. Resistin particularly has a disulfide-dependent multi-bonding structure, human resistin forms an oligomer as in murine resistin, and exists mainly as an oligomer having at least 660 kDa, a trimer having 45 kDa. An oligomeric form of human resistin is more biologically active, and therefore, shows stronger influence upon stimulation of pro-inflammatory cytokine.

Figure 22:
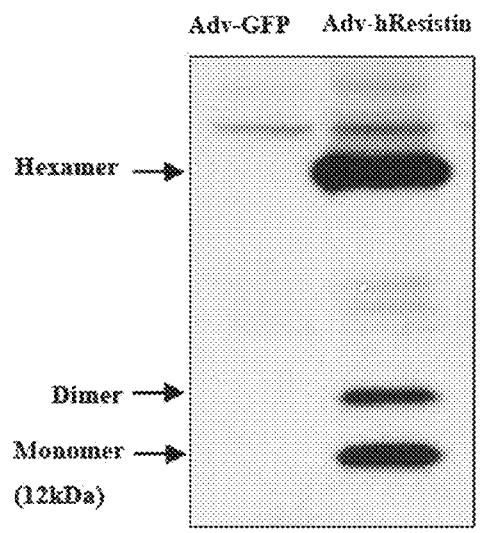
FIG. 22 illustrates results of a non-reducing SDS gel analysis of medium using HUVEC lysate infected with adenovirus resistin.

In addition, the present inventors could predict an oligomeric form of adenovirus resistin through a non-reducing SDS gel analysis of medium using human umbilical vein endothelial cells (HUVEC) lysate in which adenovirus resistin is infected, and FIG. 22 shows a total protein amount % of resistin oligomer, and a ratio of all resistins having monomer and dimer form. As such, an adenovirus expression resistin having an oligomeric form is determined to be having more effective biological influence than general bio-active recombinant resistin which is known to have protein dimer form.

A function of cAMP which regulates a function of macrophage or a relationship between PKA and NF-κB are still not defined clearly, yet recent research results report the relationship of AMP/PKA signal transduction and pro-inflammatory pathway in macrophage.

The present inventors have been revealed that a PKA inhibitor kills an activity of NF-κB induced by resistin, shows a new binding between cAMP/PKA axis and signal transduction of NF-κB, and decreases an increase of expression of cytokine which reacts with resistin.

Moreover, the present inventors regulated an activity of human resistin by suppressing an expression of CAP1 using CAP1 small interfering RNA (siRNA) in order to reveal a signal transduction pathway of resistin-CAP1 complex and CAP1 being a functional receptor for human resistin, and confirmed a decrease of cAMP concentration, an activity of protein kinase A (PKA) and nuclear factor kappa B (NF-κB), and expression of inflammatory cytokine by the suppression of CAP1 expression.

In addition, the present inventors revealed a signal transduction pathway in which human resistin and its receptor, CAP1 protein, interact each other, and confirmed the interaction between human resistin and CAP1 protein in vitro and in vivo.

Hereinafter, preferred embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

Example 1. Preparation of mFc-Human Resistin Recombinant DNA

In order to confirm a complex of resistin and a resistin receptor, a recombinant DNA which encodes mFc-conjugated human resistin protein was initially prepared.

A structure of recombinant DNA which encodes mFc and human resistin fusion protein and an expression vector were shown in FIG. 1.

In particular, in order to prepare the recombinant DNA which encodes mFc-conjugated human resistin protein shown in FIG. 1, firstly, PCR primer including HindIII and XhoI sequences (forward primer: SEQ ID NO:1. 5'-CCCAAGCTTATGGAGACAGACACACTCCTGC-TATGGGTACTGCTGCTCTGGGTTCCA GGTTC-CACTGGTGACGAGCCCAAATCTAGCGACAA-3', reverse primer: SEQ ID NO:2. 5'-CGAGCCACCGCCAC- CCGAGCCACCGCCACCCGAGCCACCGCCACCTT-TACCAGGGA GTGGGAGA-3'), and Taq polymerase were used to conduct polymerase chain reaction (PCR) to prepare the mFc-conjugated human resistin recombinant DNA.

The recombinant DNA proliferated by the PCR was cut with a restriction enzyme for HindIII and XhoI, cloned in an expression vector which is pcDNA3.1 by using T4 DNA ligase, and applied heat shock at 42° C. for 1 min. and 30 sec. so as to transfect a recombinant plasmid to *E. coli* DH5α. The transfected *E. coli* DH5α was smeared in Luria Bertani (LB) agar plate including ampicillin, cultivated in 37° C. incubator for 16 to 24 hours, and plasmid mini-prep was conducted from the *E. coli* DH5α colony generated on the LB plate. The obtained plasmid was proliferated by PCR, cut with the restriction enzyme for HindIII and XhoI to confirm insertion of mFc human resistin recombinant DNA in the expression vector which is pcDNA3.1, and a sequence analysis was performed to screen a clone which is 100% identical to the sequence of mFc human resistin recombinant DNA.

Example 2. Expression of mFc-Human Resistin Protein

In order to confirm a good expression of mFc human resistin recombinant protein in the recombinant DNA cloned in the expression vector pcDNA3.1 according to example 1, the recombinant DNA was transfected to HEK293-F cells using polyethyleneimine (PEI).

In particular, cells were seeded in a cell culture dish so that a cell density of the HEK293-F cells to become 70 to 80% at one day before the transfection. At a following day, the mFc human resistin recombinant DNA which was cloned in the expression vector which is pcDNA3.1 and the transfection inducing material, PEI, were mixed and introduced in the HEK293-F cells. After a certain time of cell cultivation, only cell culture medium was separated and concentrated. The concentrated cell culture medium was passed through the column in which beads specific to mFc (CaptureSelect Multi Species affinity matrix) are filled, and only mFc human resistin recombinant protein specifically binding to the beads was separated by using an elution buffer (0.1M Glycine-HCl, pH 2.8).

Figure 2:
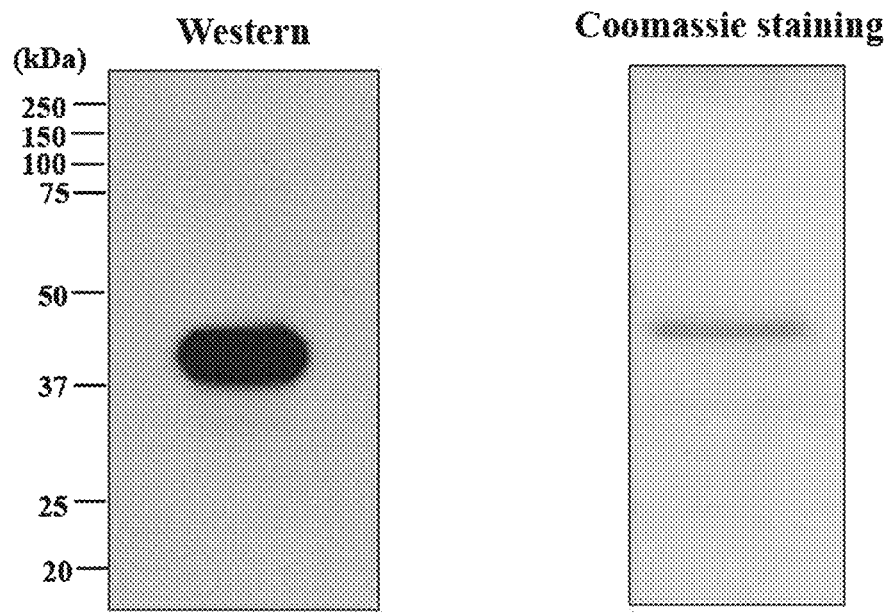
FIG. 2 illustrates results of western blot and coomassie staining to confirm the expressed mFc-human resistin protein.

A supernatant of the cultivated cell was concentrated and purified, and western blot was conducted using an anti-mFc human resistin protein antibody, of which result is shown in FIG. 2.

As shown in FIG. 2, a clear band indicating mFc-human resistin protein was confirmed in a range from 37 kDa to 50 kDa.

Example 3. Confirmation of Resistin Receptor

In order to find a receptor protein which binds to mFc human resistin recombinant protein, THP-1, HUVEC, and human ascular smooth muscle cells (VSMCs) were cultivated and classified by applying fluorescence-activated cell sorting (FACS). A protein was extracted from the cells, and western blot was performed by using the purified mFc human resistin recombinant protein as a primary antibody.

In particular, all proteins were extracted from THP-1, HUVEC, and human VSMC cell, and then, protein electrophoresis (SDS-PAGE; Sodium Dodecyl Sulfate Polyacrylamide gel electrophoresis) was performing with 8% separating acrylamid gel. The proteins separated by the protein electrophoresis were transferred to polyvinylidene fluoride (PVDF) membrane, and then, reacted together with PVDF membrane by using mFc human resistin recombinant protein as a primary antibody.

Subsequently, among the above three cell proteins, the protein which binds to mFc human resistin recombinant protein was confirmed by using an anti-mFc-HRP secondary antibody (anti-mouse Fc specific peroxidase conjugate) specific to mFc.

Figure 3:
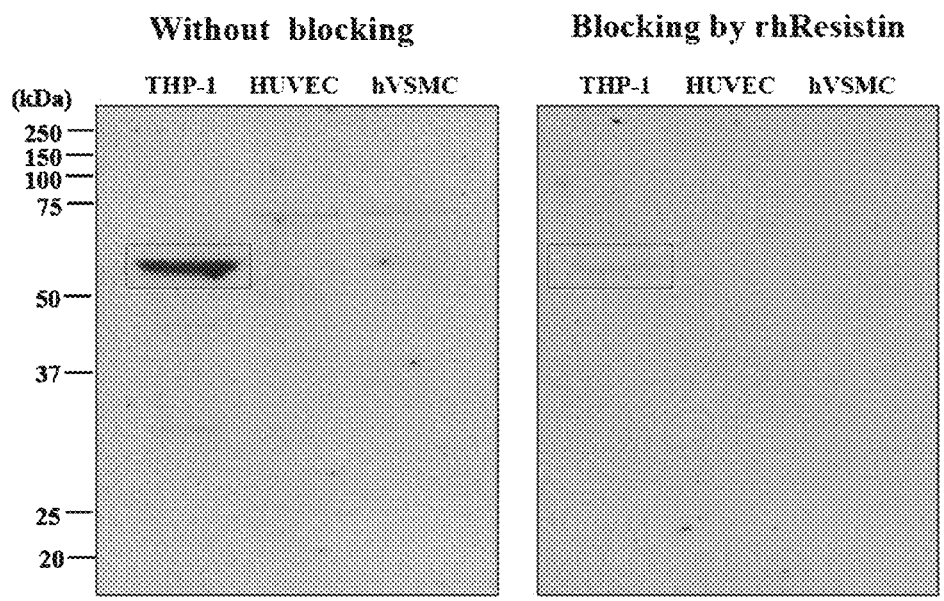
FIG. 3 illustrates results of western blot of a protein complex to which mFc-human resistin protein binds in THP-1, HUVEC, and VSMC.

As shown in the results of western blot in FIG. 3, the band was found in around a size of 55 kDa only in THP-1 cell lysate among all lysates of each cell, and this band was disappeared when blocked by recombinant human resistin protein.

A molecular binding of mFc-conjugated human resistin protein in THP-1 was confirmed through the western blot results, and immuno-precipitation pull down assay was performed believing that the human resistin receptor is in THP-1 cells.

In particular, all proteins were extracted from the THP-1 cells, and then, reacted with mFc human resistin recombinant protein at 4° C. for one day. Agarose beads specific to mFc were mixed with the complex of THP-1 cell protein and mFc human resistin protein, immuno-precipitation was conducted at 4° C. for one day, and centrifugation was performed to remove a supernatant leaving only the beads. In order to remove non-specific proteins which did not bind to the beads, the beads were washed with radioimmunoprecipitation assay (RIPA) buffer, 1× electrophoresis sample buffer was introduced, boiled at 100° C. for 5 min., and again, centrifugation was performed to take only a supernatant excluding the beads. A protein electrophoresis (SDS-PAGE; Sodium Dodecyl Sulfate Polyacrylamide gel electrophoresis) was performed for the supernatant using 8% separating acrylamid gel, the gel was stained with coomassie brilliant blue 8250, and the results were illustrated in FIG. 4.

Figure 4:
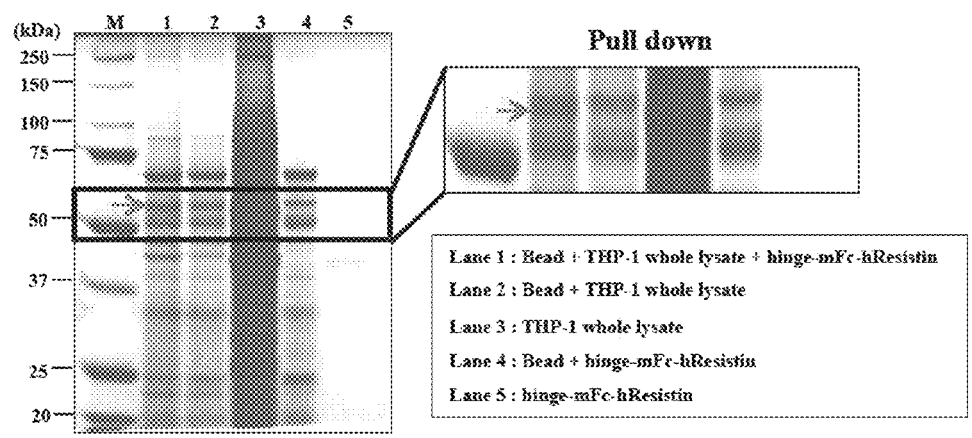
FIG. 4 illustrates results of pull down assay of immunoprecipitation of THP-1 cells extract and resistin for cloning a human resistin receptor.

From results of FIG. 4, the band for the complex to which mFc-conjugated human resistin protein binds was clearly appeared in around 55 kDa among THP-1 cell lysates. The purified protein appeared in around 55 kDa which is predicted to be resistin receptor was cut, mass spectrometry was performed with MALDI-TOF, and as a result of confirming the receptor, it was found to be adenylyl cyclase-associated protein 1 (CAP1) which was previously named.

Example 4. Confirmation of Position of CAP1 Protein

It is already known that CAP protein can be found and preserved anywhere. Further, the present inventors have found mRNA which encodes CAP1 in various rabbit tissues based on the report that rabbits are more suitable than rats for the physiological research for humans.

In particular, tissues were torn off from various organs in rabbits, the tissues were ground with mortar, and all RNAs were extracted from the tissues by introducing Tirzol. cDNA was synthesized at 42° C. by using the all RNA 1 μg, oligo-dT primer, dNTP mix, Rnase inhibitor, and RTase. PCR was performed with primer specific to CAP-1, $MgCl_2$, dNTP mix, and Taq polymerase by using the cDNA synthesized from each tissue as a template, electrophoresis was conducted with 1.8% agrose gel, and the results of confirming CAP-1 expression for each tissue were illustrated in FIG. 5.

Figure 5:
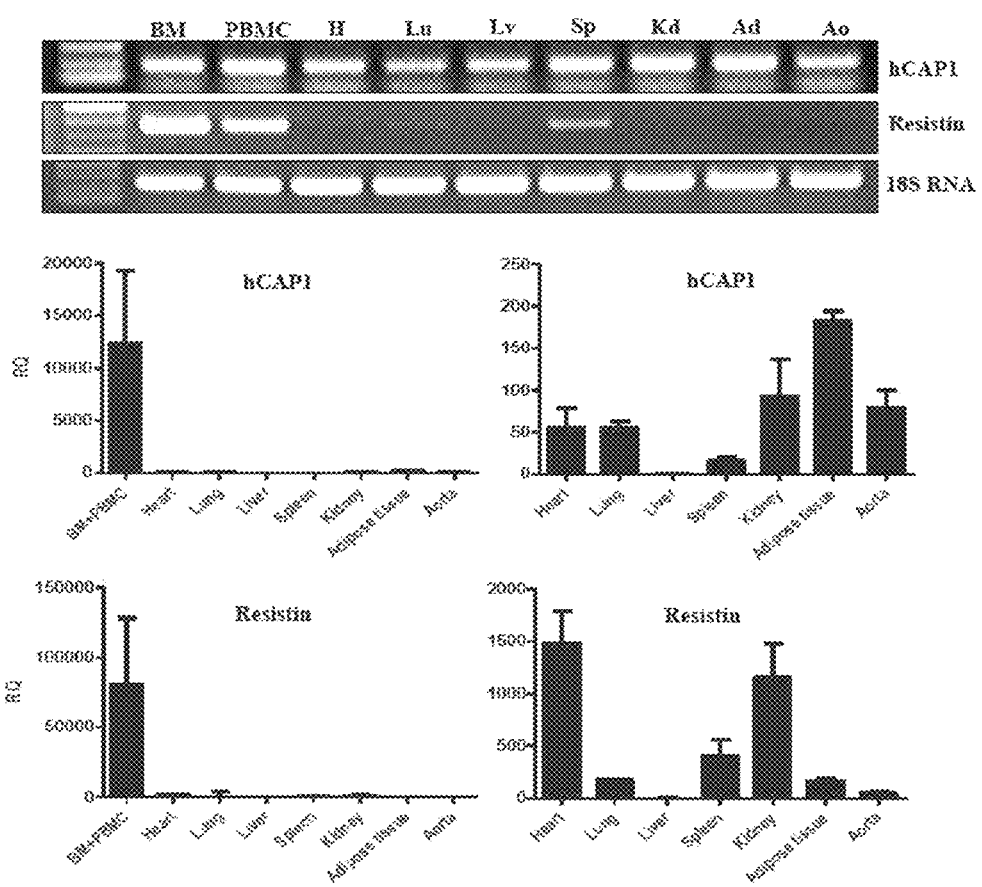
FIG. 5 illustrates results of conventional PCR and real time PCR which show a degree of expression of CAP1 in rabbit tissue cells.

FIG. 5 indicates that CAP1 is expressed in any rabbit tissue cells, and that, the expression level is different by each tissue. In particular, a high expression was shown in peripheral blood mononuclear cell (PBMC) of rabbit, showing a similarity with an expression pattern of human resistin.

The above studies provide proofs that CAP1 and human resistin molecules were related to various inflammatory-related processes through monocyte activity.

In general, a position of CAP1 protein is species-specific, and recently, there was the research reporting that CAP1 is related to a THP-1 cell membrane.

In the present invention, proven were the fact that CAP1 is located in a cell membrane of human mononuclear leukocyte and the hypothesis that CAP1 protein which exists in the cell membrane binding to human resistin through western blot, immunofluorescent stain and flow cytometry.

The protein was extracted from the cell membrane and cytosol of THP-1 cells, protein electrophoresis (SDS-PAGE) was performed, the protein was transferred to PVDF membrane, and the PVDF membrane was reacted with human CAP-1 antibody, thereby confirming an expression of human CAP-1 in a cell membrane and cytoplasm, of which results were illustrated in FIG. 6.

As shown in the results of western blot in FIG. 6, CAP1 protein was found in cell membrane, and immunofluorescence staining results showed that CAP1 proteins were dispersed around cytoplasm, especially concentrated in a human monocyte cell membrane.

FIG. 7 shows the flow cytometry results of classifying THP-1 cells to which human CAP1 monoclonal antibody binds, suggesting a possibility that resistin concentration-dependently stimulates CAP1 to migrate to a cell membrane.

In particular, THP-1 cells including control THP-1 cells (no stimulation), and the THP-1 cells in which human recombinant resistin protein was stimulated with various concentrations were recovered, an isotype control antibody which becomes an origin of a primary antibody was mixed and reacted with the control cells, while a human CAP-1 monoclonal antibody was mixed and reacted with the THP-1 cells which was stimulated with human recombinant resistin protein. The cell was washed with FACS buffer, the cell was reacted with anti-mouse IgG Alexa 488 fluorescence secondary antibody which can recognize human CAP-1 monoclonal antibody, and the THP-1 cells to which human CAP-1 monoclonal antibody binds were classified by using FACS equipment.

From the above, it is obvious that extracellular human resistin binds to CAP1 protein in a plasma membrane of human monocyte.

Example 5. Confirmation of Binding Between Human Resistin and CAP1 Protein 5-1. Double-Immunofluorescence THP-1 cells were treated with human recombinant resistin, the cells were placed on a slide glass, the cells were blocked with PBS solution containing 0.5% Triton X-100 and 1% BSA, and permeabilization was performed. THP-1 cells were doubly stained with a human resistin antibody and human CAP-1 antibody, a secondary antibody having different fluorescence for recognizing resistin and CAP-1 was attached to the THP-1 cells which were stained with a primary antibody, and it was confirmed through confocal microscopy that resistin and CAP-1 were stained in the same position in THP-1 cell, of which results were illustrated in FIG. 8.

Figure 8:
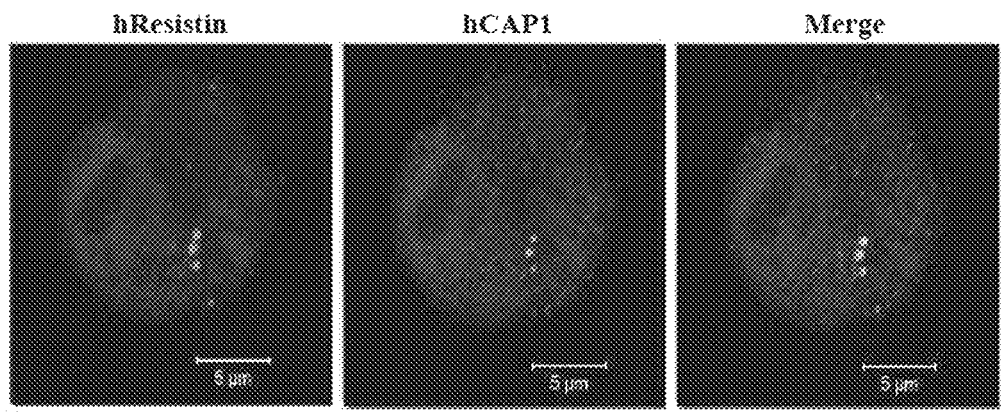
FIG. 8 illustrates results of double-immunofluorescence which shows that resistin and CAP1 are in the same position.

FIG. 8 shows that resistin and CAP1 are in the same position in THP-1 cells in which recombinant human resistin was treated as a result of confirming labeling by double-immunofluorescence. Resistin and CAP1 showed similar distribution and similar fluorescence strength, strongly indicating that they exist in the same position.

5-2. Co-Immuno-Precipitation Experiment

In order for clearer confirmation of a direct interaction between human resistin and CAP1, co-immuno-precipitation experiment was performed. Immuno-precipitation was performed with an anti-human resistin antibody for the all cell extracts of the THP-1 cells, immune-blot was conducted with CAP1 antibody, and the experiment was performed vice versa.

In particular, all proteins were extracted from THP-1 cells, the extracted protein was immuno-precipitated with anti-human CAP-1 antibody at 4° C. for one day. To the control group, mouse IgG which becomes an origin of anti-human CAP-1 antibody was introduced. To a complex of THP-1 protein and anti-human CAP-1 antibody, protein G agarose beads were introduced and reacted, and the supernatant was removed via centrifugation leaving the beads. Thereafter, 1× electrophoresis sample buffer was introduced to the beads, boiled at 100° C. for 5 min., and again, centrifugation was performed to take only a supernatant excluding the beads. A protein electrophoresis (SDS-PAGE; Sodium Dodecyl Sulfate Polyacrylamide gel electrophoresis) was performed for the supernatant using 8% separating acrylamid gel, the gel was transferred to PVDF membrane, and western blot was conducted with an anti-human resistin antibody and anti-human CAP-1 antibody to confirm a binding between human resistin and human CAP-1, of which results were illustrated in FIG. 9.

Figure 9:
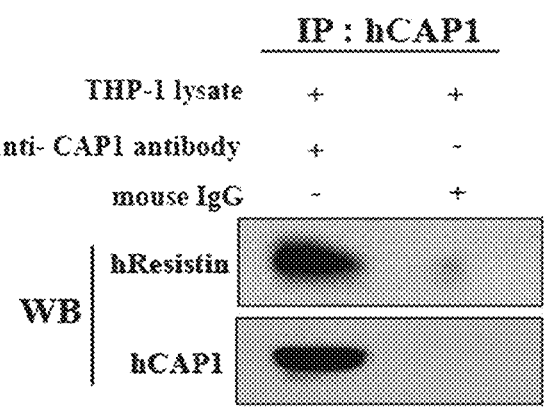
FIG. 9 illustrates results of co-immunoprecipitation of human resistin and CAP1.

As a result, as shown in FIG. 9, co-precipitation of human resistin and CAP1 in THP-1 can be confirmed.

5-3. Far Western Blotting

In order to confirm a direct binding of resistin and CAP1 in vitro, far western blotting was performed. In particular, the purified mFc-human resistin protein was prepared, and it was transferred to cell membrane with standard western blot. The protein in a cell membrane was denatured and renatured. Subsequently, the cell membrane was cultivated together with recombinant human CAP1.

In particular, a protein electrophoresis (SDS-PAGE) was performed for the purified mFc human resistin recombinant protein, and the gel was transferred to PVDF membrane. In order to renature the denatured protein, the membrane was reacted in denaturing/renaturing buffer, and blocked with PBST containing 5% skim milk at room temperature for 1 hour. The membrane was reacted with recombinant human CAP-1 protein, and western blot was performed with anti-human CAP-1 antibody. Detection in the position of resistin, not the position of CAP-1, was confirmed since anti-human CAP-1 antibody should recognize a complex of resistin and CAP-1 if recombinant human CAP-1 protein and mFc human resistin recombinant protein were bound to each other.

Figure 10:
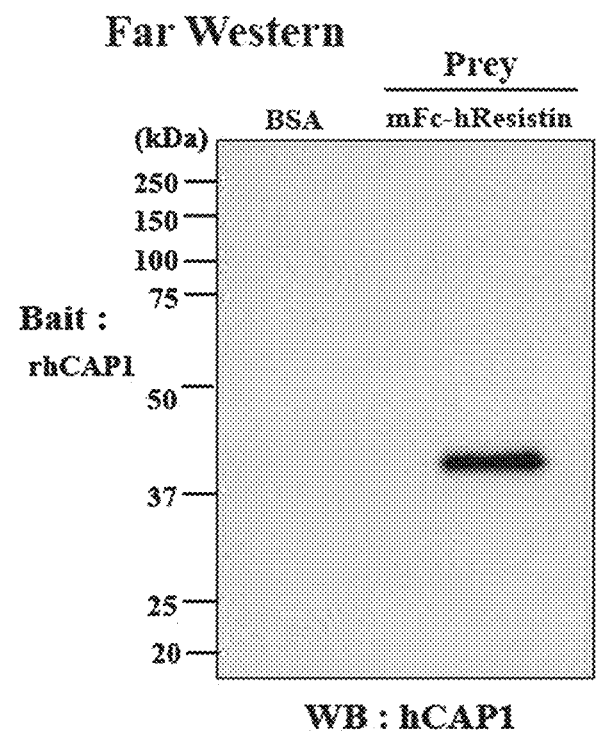
FIG. 10 illustrates results of far western blotting of human CAP1 and resistin.

The results of above far western blotting were shown in FIG. 10. As shown in FIG. 10, CAP1 was confirmed in the position in which mFc-human resistin protein is located.

Accordingly, it is obvious from the results that resistin and CAP1 directly interact and form a complex.

5-4. Receptor-Binding Competition Study

As in the general enzyme-linked immunosorbent assay (ELISA) experiment, recombinant CAP1 protein was prepared by diluting with photoresist in each well. Each plate was cultivated with a certain amount of mFc-human resistin, and the measurement was made to the mFc-human resistin to which recombinant CAP1 binds.

In particular, recombinant CAP-1 proteins were coated in the same concentration in 96-well plate. In the well coated with CAP-1 protein, mFc human resistin recombinant protein was supplied in an amount of 0.05, 0.5, and 1 ug, each well was treated with an increasing concentration of recombinant human resistin protein, and cultivated for 2 hours. It was then treated with an anti-mFc-HRP antibody which enables detection of mFc human resistin recombinant protein, colorized by introducing tetramethylbenzidine (TMB), and absorbance was measured at 450 nm, of which results were illustrated in FIG. 11.

Figure 11:
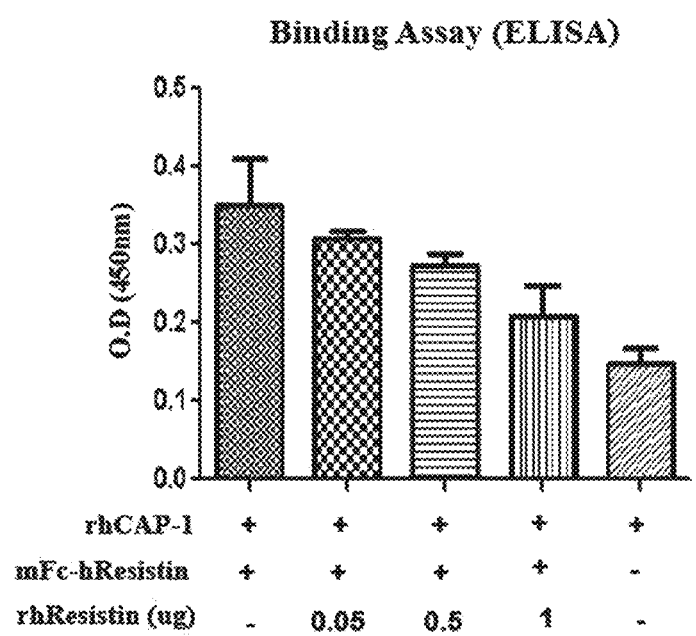
FIG. 11 illustrates results of ELISA experiment to measure competitive bindings between mFc-human resistin protein and recombinant resistin towards recombinant CAP1.

As shown in FIG. 11, it was confirmed that mFc-human resistin migrates by recombinant human resistin, and the fluorescence signal decreased in proportion to an amount of competitive recombinant protein.

Furthermore, human resistin is over-expressed in THP-1 cells by using resistin adenovirus, and recombinant CAP-1 protein was treated to cultivate the cells. The THP-1 cells were recovered, and an isotype control antibody which becomes an origin of a primary antibody was mixed and reacted with the control cells, while human integrin-β1 antibody was mixed and reacted with the THP-1 cells in which resistin adenovirus was over-expressed. The cells were marked with a secondary antibody having fluorescence which can recognize integrin-β1 antibody, and then, the number of THP-1 cells to which integrin-β1 antibody binds was measured by using FACS equipment.

Figure 12:
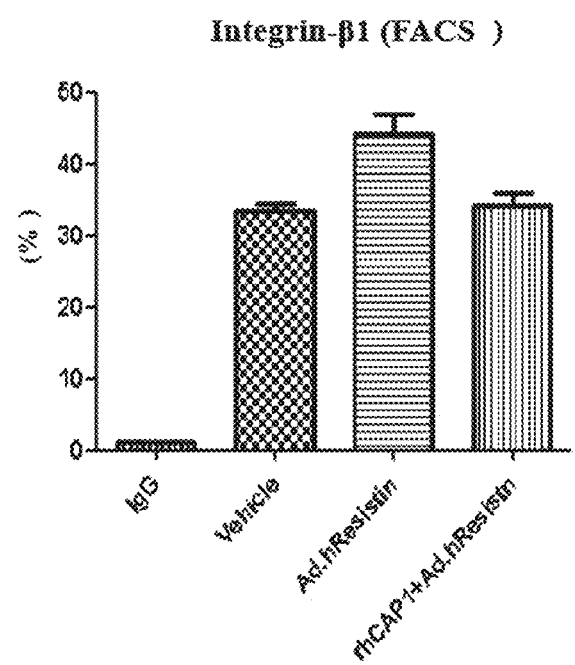
FIG. 12 illustrates results of FACS experiment to confirm an influence of recombinant CAP1 protein on integrin-β1 expression of resistin.

As shown in FIG. 12, since CAP-1 is a receptor for resistin, when resistin was over-expressed by using adenovirus, and then, reacted with recombinant CAP-1, the recombinant CAP1 behaved as a neutral antibody for resistin, therefore suppressed binding of the over-expressed resistin to human monocyte as well as an expression of integrin-β1 by PBMC which occurs as a response to resistin stimulus.

All of the above experimental results prove the fact that CAP1 and resistin directly interact to regulate a function of monocyte and form a complex.

Example 6. Confirmation of Resistin-CAP1 Complex

CAP1 is known as a multi-functional molecule including domains related to actin bonding, adenylyl cyclase association in yeast, SH3 binding and oligomer formation.

The three structural and functional domains of CAP1 were indicated in FIG. 13.

The present inventors believed that actin binds to carboxyl-terminal of CAP1, and a signal molecule binds to the amino-terminal, while resistin binds to a proline-rich domain of CAP1, and as such, tried to understand the structure of SH3 binding domain of CAP1 in order to prove this hypothesis.

Homology modeling is the most simple and trustworthy methodology in predicting molecular structure. A foundation of this modeling is based on the fact that proteins having similar sequence tend to be fold in a similar structure. Generally, 30% of the sequence should be identical in order to make a useful model, and the proteins having 25% of identical sequence fold in a similar structure.

Figure 14:
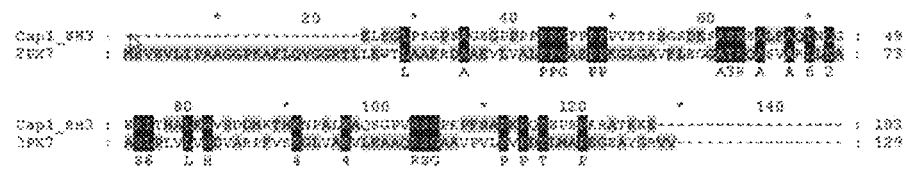
FIG. 14 illustrates a comparison of sequences between *Thermus thermophilus* HB8 (2PX7) and CAP1.
Figure 15:
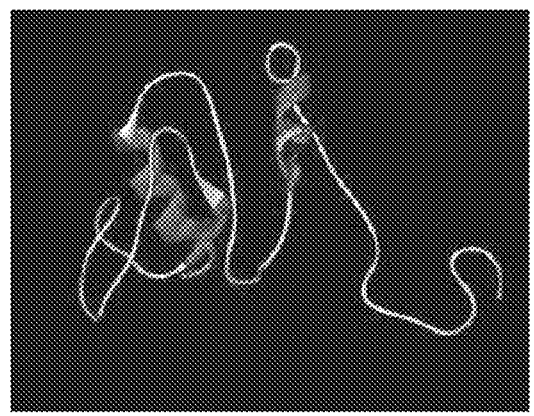
FIG. 15 illustrates a finally-predicted diagram showing poly-proline SH3 binding domain of CAP1 confirmed by using Discovery Studio 2.5 (Accelrys Inc.).

A sequence of proline-rich domain of CAP1 (SEQ ID NO:3) is identical to the one of cytidyly transferase originating from *Thermus thermophilus* HB8 (2PX7; SEQ ID NO:4) (FIG. 14) by 20%, and similar by 32%. FIG. 15 shows a finally-predicted diagram showing poly-proline SH3 binding domain of CAP1 confirmed by using Discovery Studio 2.5 (Accelrys Inc.).

In order to confirm the predicted structure of resistin-CAP1 complex, protein-protein docking simulation and score function analysis were performed based on surface geometry. Several three-dimensional binding structures between resistin trimer and CAP1 were experimentally revealed by using docking algorithm ZDOCK based on pairwise shape complementarity (PSC) function.

Example 7. Confirmation of Resistin Binding Domain of CAP1

7-1. Preparation of Each Domain Deficient Mutation Recombinant Vector of CAP1

Figure 16:
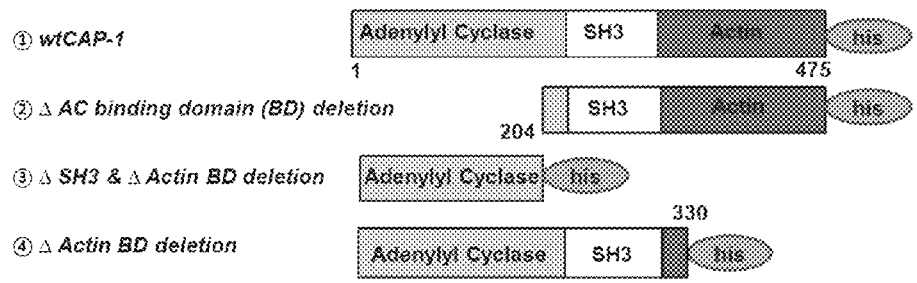
FIG. 16 illustrates a schematic diagram showing a structure of three deficient mutation genes of human CAP1.
Figure 17:
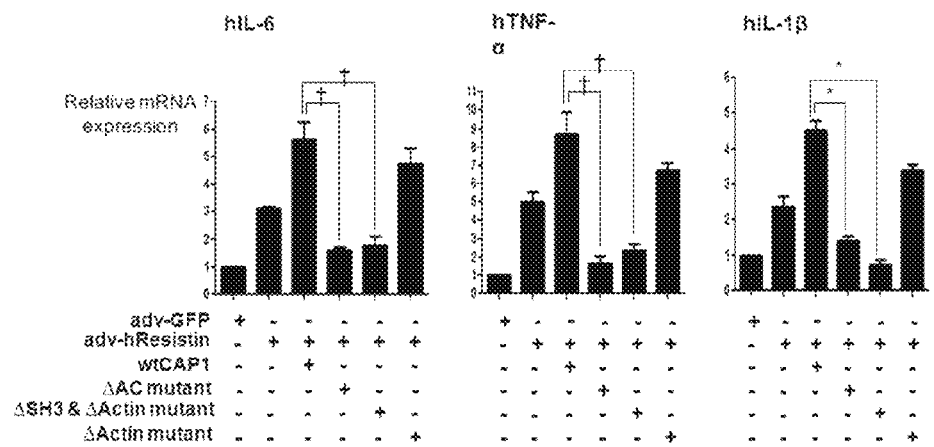
FIG. 17 illustrates a diagram confirming a relative mRNA expression value for each inflammatory cytokines induced by resistin after over-expressing CAP1 mutation gene of FIG. 17 in THP-1 cells.

In order to reveal which domain of CAP1 binds to resistin, preparation of a mutation recombinant vector (SH3 actin BD deletion) was made in which adenylyl cyclase (AC) binding domain deficient mutation (AC binding domain [BD] deletion), actin binding domain deficient mutation (AC binding domain [BD] deletion), SH3 binding domain and actin binding domain were all deficient by using a lentivirus vector. The structure of these genes was illustrated in FIG. 16. Each CAP1 mutation gene was over-expressed in THP-1 cells, secretion of pro-inflammatory cytokine was induced by resistin transferred through an adenovirus vector, and the value was measured. There was no substantial change in production of inflammatory cytokine in Δactin BD deletion mutant after stimulating with resistin, whereas the cytokine production in ΔAC BD deletion mutant and ΔSH3Δactin BD deletion mutant was greatly suppressed (refer to FIG. 17).

The above results indicate the fact that actin binding domain of CAP1 is not essential for inflammation reaction of the monocyte induced by resistin as well as the fact that other two domains were critical for resistin ligand binding and/or receptor signal transduction.

7-2. Binding Assay of CAP1 and rhResistin when Each Domain Deficient Mutation of CAP1 was Expressed In order to confirm the exact binding position of resistin in CAP1, CAP1 mutation was performed in vitro, and then, binding assay of rhResistin was conducted. His-tagged CAP1 mutation gene was over-expressed in 293A cells, treated with rhResistin, and then, the all cell extract was immuno-precipitated with anti-His antibody.

Figure 18:
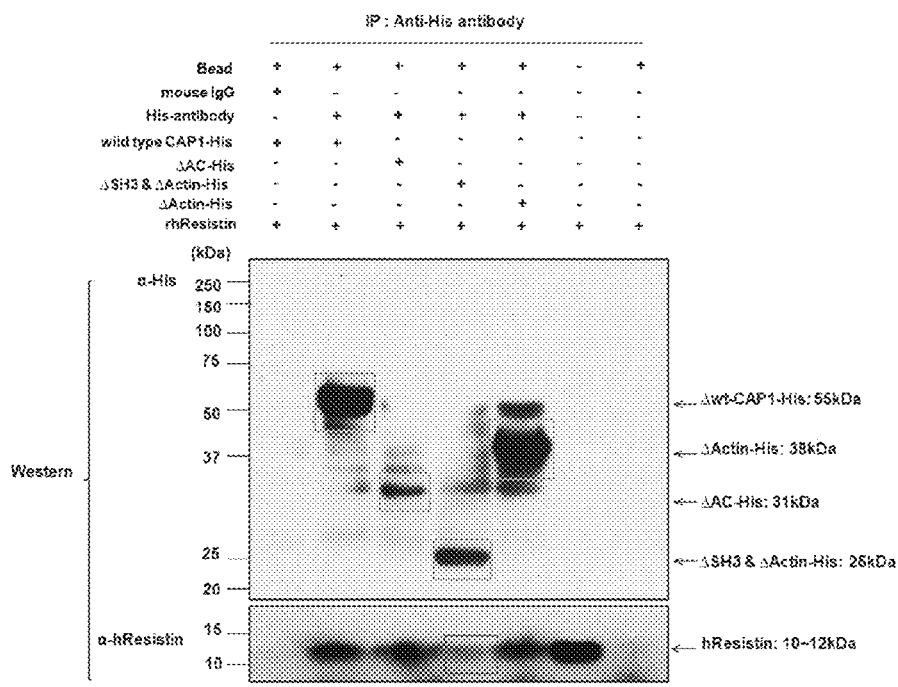
FIG. 18 illustrates a diagram showing results of in vitro binding assay between rhResistins when each CAP1 mutation gene is expressed.

Western blot was performed for the samples by using an anti-resistin antibody and an anti-His antibody. When SH3 actin BD deletion mutant was expressed, the band shown in around 12 kDa was disappeared after treating with rhResistin (refer to FIG. 18). In contrast, when AC BD deletion mutant or actin BD deletion mutant was expressed, rhResistin band was observed.

The above results show that human resistin binds through a proline-rich SH3 binding domain, and that adenylyl cyclase domain does play a critical role in receptor signal transduction.

Example 8. Confirmation of Resistin Signal Transduction Pathway

In order to confirm a function of resistin-CAP1 complex for intracellular signal transduction pathway, the following experiments were conducted.

8-1. Confirmation of Change in cAMP Amount

A change in cAMP amount by resistin was measured by using cyclic AMP (cAMP) analysis kit. Firstly, a supernatant was obtained by dissolving THP-1 cells which was stimulated with recombinant resistin. A primary antibody solution for cAMP measurement was introduced to the well of plate for cAMP measurement, and coated at room temperature for 1 hour. Each well was washed with washing buffer, and then, the supernatant obtained in the standard solution and the THP-1 cells were added to the well. To each well, cAMP conjugate was added, and then, cultivated at room temperature for 2 hours. A substrate solution was introduced and reacted at room temperature for 30 min., and then, the reaction was ceased by adding a stop solution. Absorbance was measured at 450 nm by using a microplate reader, of which results were illustrated in FIG. 19.

Figure 19:
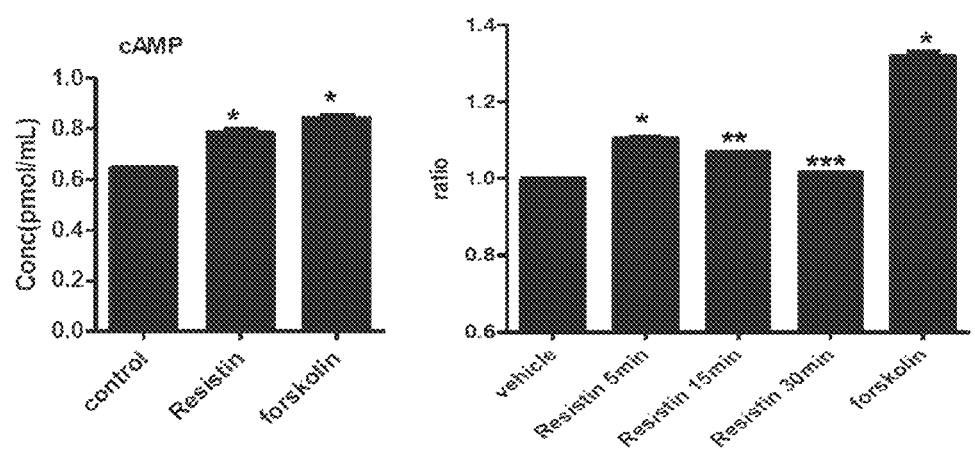
FIG. 19 illustrates a change in cAMP concentration in accordance with resistin treatment.

As shown in FIG. 19, cAMP was increased by resistin, and reached its maximum in 5 min. after resistin treatment.

8-2. Confirmation of Change in PKA and NF-κB Amount

Further, the present inventors assessed a change in activity of protein kinase A (PKA) and nuclear factor kappa B (NF-κB) by resistin. In particular, THP-1 cells were stimulated with recombinant resistin protein or human resistin was over-expressed with resistin adenovirus, and then, cytosol and nuclear protein were separated from each cell. Western blot was performed for the separated each protein, and by using phospho-vasodilator-stimulated phosphoprotein (p-VASP)(Ser157) antibody which recognizes phosphorylation of VASP which is a substrate of PKA and P50 and P65 antibodies which are the two subtypes of NF-κB, the changes of PKA and NF-κB were confirmed, of which results were illustrated in FIG. 20.

Figure 20:
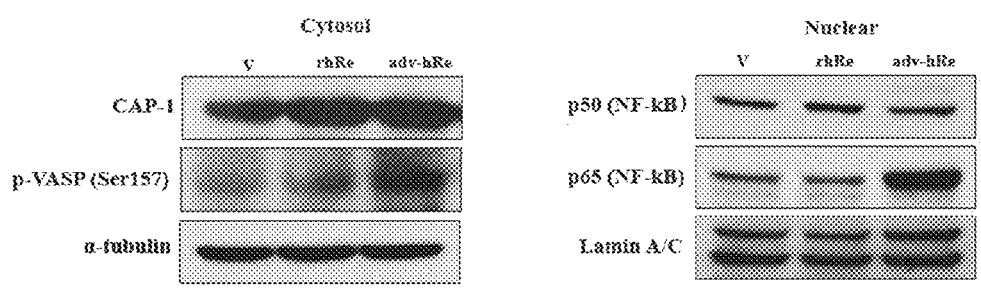
FIG. 20 illustrates a change in activity of PKA and NK-κB in accordance with resistin treatment.

As shown in FIG. 20, resistin was shown to increase activity of both PKA and NF-κB. In addition, the resistin expressed by adenovirus showed more powerful effect than recombinant resistin.

8-3. Confirmation of Influence of Inflammatory Cytokine on mRNA

After over-expressing human resistin in THP-1 cell by using resistin adenovirus, the cell was recovered, and all RNAs were extracted with a Trizol solution. cDNA was synthesized at 42° C. by using the all RNA 1 μg, oligo-dT primer, dNTP mix, Rnase inhibitor, and RTase. A conventional PCR was performed with primers specific to inflammatory cytokine gene, $MgCl_2$, dNTP mix, and Taq polymerase by using the synthesized cDNA as a template, and electrophoresis was conducted for the PCR product in agrose gel, confirming each gene's expression. Further, a real time PCR was performed for each gene by using SYBR green.

As shown in FIG. 21, expression of integrin-β1 and inflammatory cytokines, such as IL-6 (interleukin 6), TNF-α (tumor necrosis factor-α), and IL-1 (interleukin 1), is accelerated by resistin, and the effect can be furthered by the resistin expressed with adenovirus.

The above results are based on the fact that the structure of resistin is important in showing a satisfactory reaction when regulating a macrophage function. Resistin particularly has a disulfide-dependent multi-bonding structure, human resistin forms an oligomer as in murine resistin, and exists mainly as an oligomer having at least 660 kDa, a trimer having 45 kDa. An oligomeric form of human resistin is more biologically active, and therefore, shows stronger influence upon a stimulation of pro-inflammatory cytokine.

8-4. Confirmation of Formation of Oligomer of Resistin

After over-expressing human resistin in human umbilical vein endothelial cells (HUVEC) by using resistin adenovirus, all cell proteins were extracted, and protein electrophoresis (SD S-PAGE) and western blot were performed under non-reducing condition, thereby confirming formation of oligomer of resistin using anti-human resistin antibody, of which results were illustrated in FIG. 22.

FIG. 22 shows a total protein amount % of resistin oligomer, and a ratio of all resistins having monomer and dimer form. As such, adenovirus expression resistin having an oligomeric form is determined to be having more effective biological influence than general bio-active recombinant resistin which is known to have protein dimer form.

8-5. Confirmation of Effect of PKA Inhibitor on Resistin's Influence

In order to confirm signal transduction of a cAMP/PKA axis and NF-kB by resistin, THP-1 cells were pre-treated with a PKA inhibitor (KT5720), and then, the THP-1 cells were stimulated with resistin adenovirus. Cytosol and nuclear proteins were extracted, western blot was performed, and a change in PKA and NF-κB was confirmed by using p-VASP (Ser157) antibody and p50 and p65 antibodies, of which results were illustrated in FIG. 23.

Figure 23:
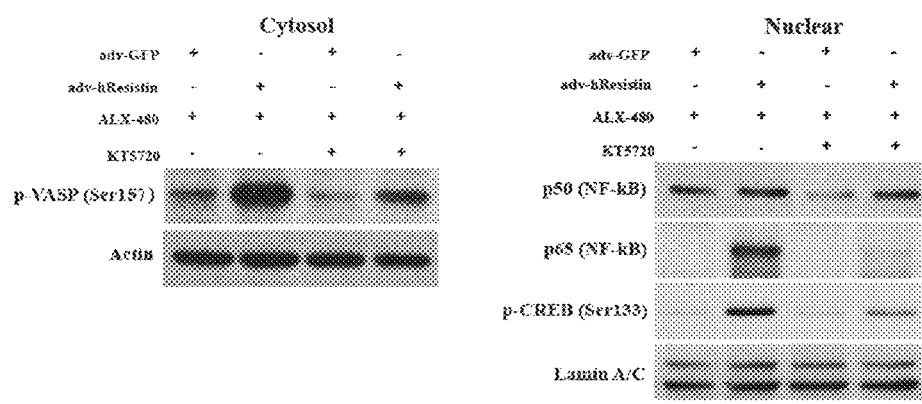
FIG. 23 illustrates results of experiment showing an effect of a PKA inhibitor for resistin in cytoplasm and cell nucleus.

As shown in FIG. 23, a PKA inhibitor kills an activity of NF-kB induced by resistin, showing a new binding in signal transduction of a cAMP/PKA axis and NF-kB.

Further, after pre-treating the THP-1 cells with a PKA inhibitor, the THP-1 cells were stimulated with resistin adenovirus. After recovering the cells, all RNAs were extracted with a Trizol solution, and cDNA was synthesized at 42° C. by using the all RNA 1 μg, oligo-dT primer, dNTP mix, Rnase inhibitor, and RTase. A real time PCR was performed for each gene with cytokine gene-specific primers and SYBR green by using the synthesized cDNA as a template, of which results were illustrated in FIG. 24.

Figure 24:
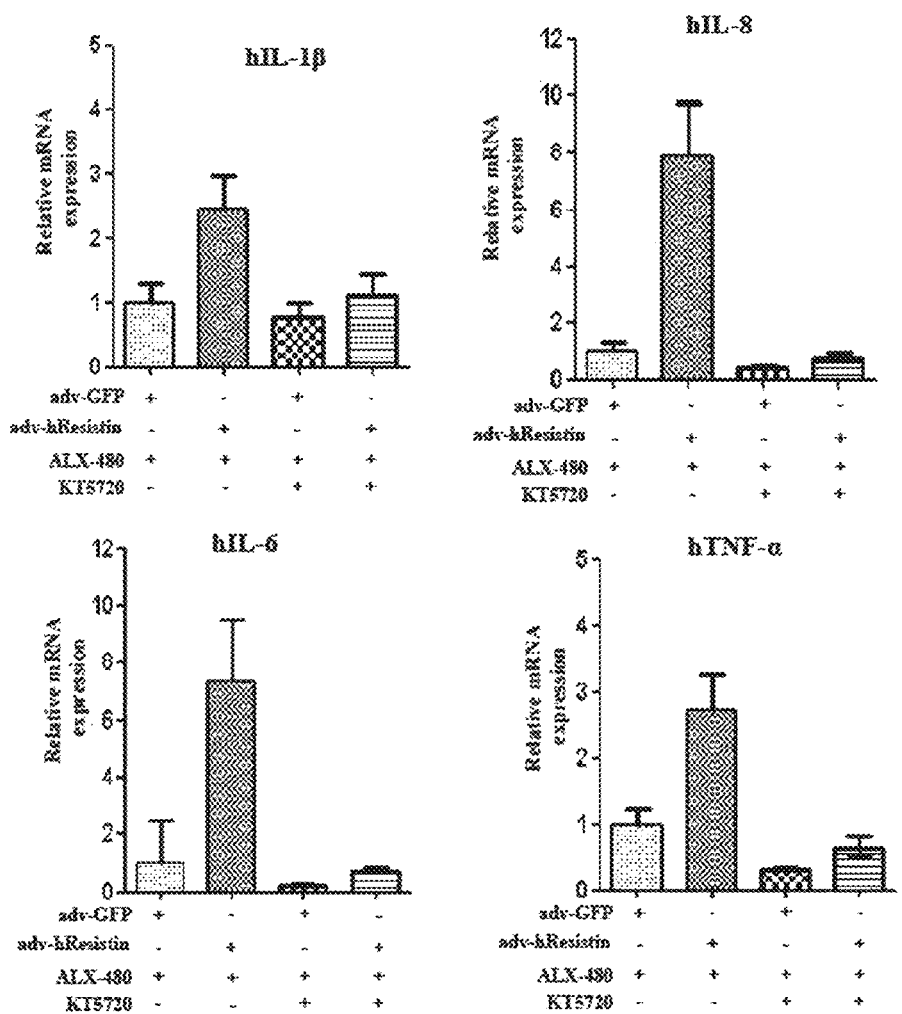
FIG. 24 illustrates an effect of a PKA inhibitor which suppresses an expression of cytokine induced by resistin.

As shown in FIG. 24, a PKA inhibitor also decreases an increase of expression of cytokine which reacts to resistin. The above experimental results provide the proof that an influence of cAMP is dependent on PKA in resistin-induced cytokine secretion in macrophage strain.

A function of cAMP which regulates a function of macrophage or a relationship between PKA and NF-κB are still not defined, yet recent research results report the relationship of AMP/PKA signal transduction and pro-inflammatory pathway in macrophage.

Example 9. Confirmation of Function of CAP1 as Receptor for Resistin

In order to confirm whether CAP1 is a functional receptor in a sense of biology, the present inventors assessed an effect of expression modification of CAP1 in a resistin-stimulated intracellular signal and an inflammation-inducing effect of mononuclear leukocyte.

9-1. Administration of CAP1 siRNA

Protein and RNA were extracted from THP-1 cells in which expression of human CAP-1 gene was suppressed with CAP-1 gene-specific siRNA. Western blot was performed, a change of PKA and NF-κB was confirmed by using p-VASP (Ser157) antibody and p50 and p65 antibodies, and after synthesizing cDNA from the extracted RNA, an effect by CAP-1 gene suppression was confirmed through real time PCR for each gene by using gene-specific primers and SYBR green, of which results were illustrated in FIG. 25 to FIG. 28.

Figure 25:
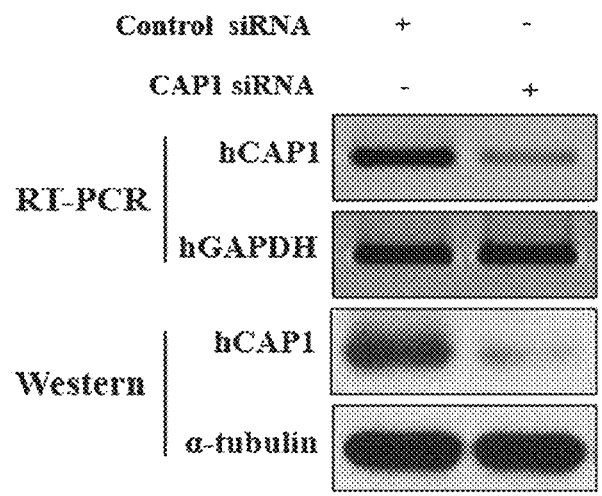
FIG. 25 illustrates an effect of suppression of CAP1 expression using CAP1 siRNA in THP-1 cells.
Figure 26:
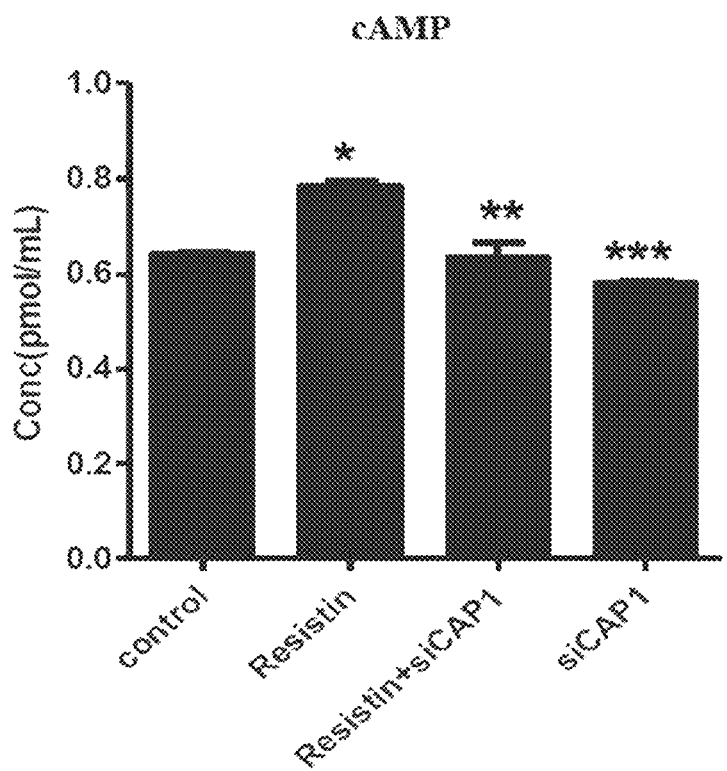
FIG. 26 illustrates a change in cAMP concentration in accordance with suppression of CAP1 expression.

FIG. 25 shows a suppression effect of CAP1 expression by using specific siRNA in THP-1 cells. According to FIG. 26, it was shown that an increase of cAMP concentration by resistin decreases when CAP1 expression is suppressed by using siRNA.

Figure 27:
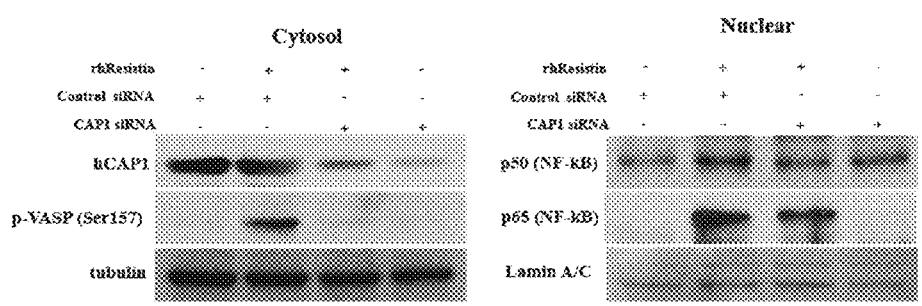
FIG. 27 illustrates suppression of activity of PKA and NF-κB in accordance with a suppression of CAP1 expression.
Figure 28:
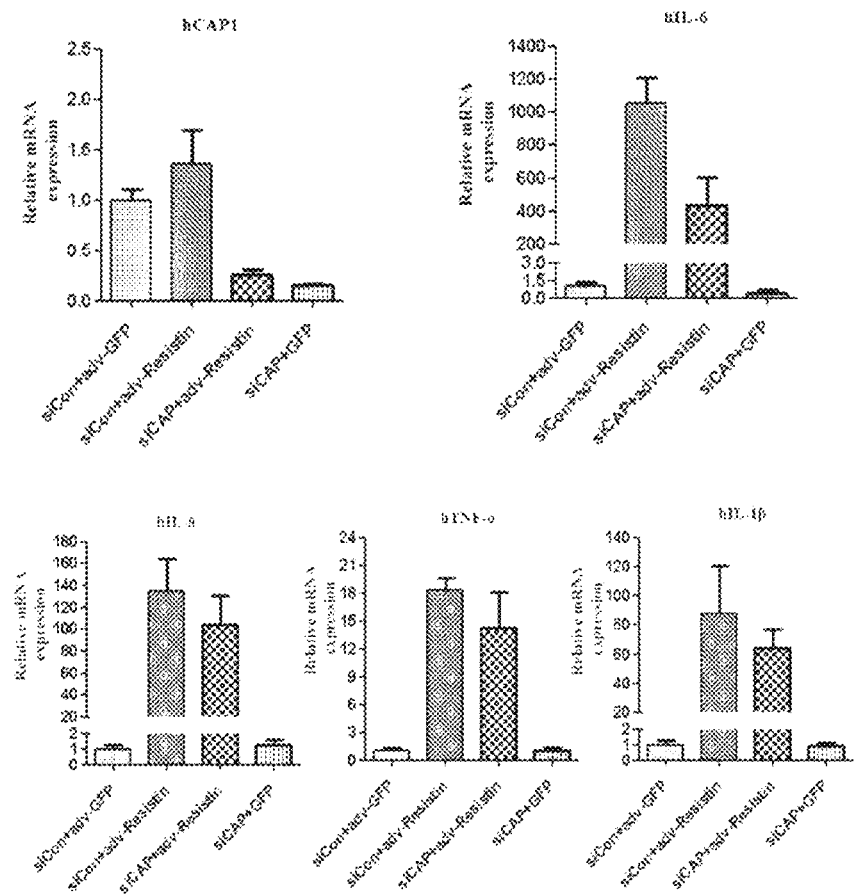
FIG. 28 illustrates suppression of expression of inflammatory cytokines in accordance with suppression of CAP1 expression.
Figure 29:
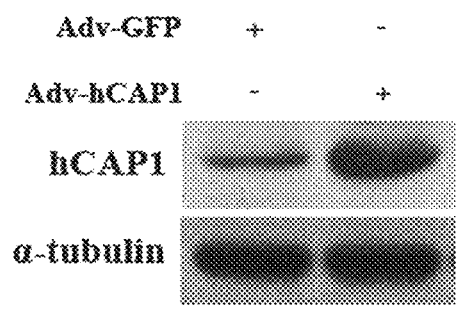
FIG. 29 illustrates an over-expression of CAP1 by adenovirus.
Figure 30:
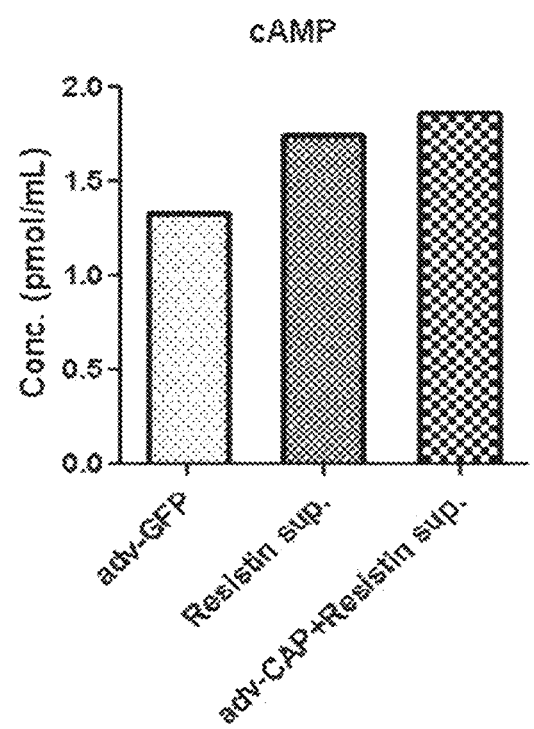
FIG. 30 illustrates a change in cAMP concentration in accordance with an over-expression of CAP1.
Figure 31:
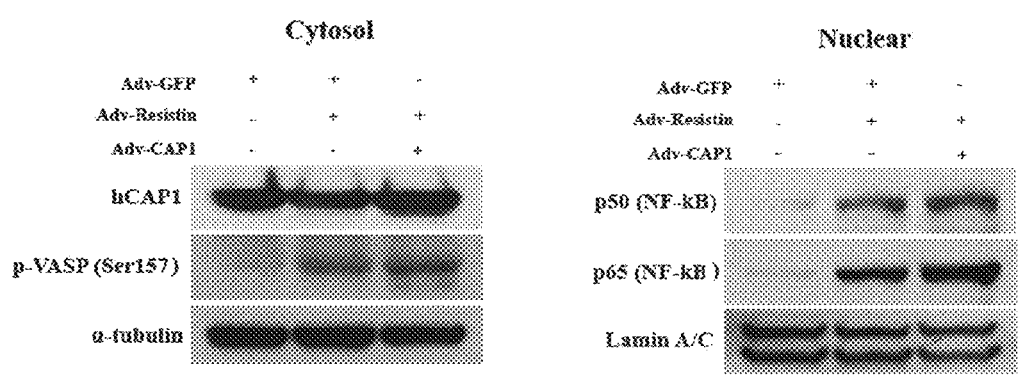
FIG. 31 illustrates an increase of activity of PKA and NF-κB in accordance with an over-expression of CAP1.
Figure 32:
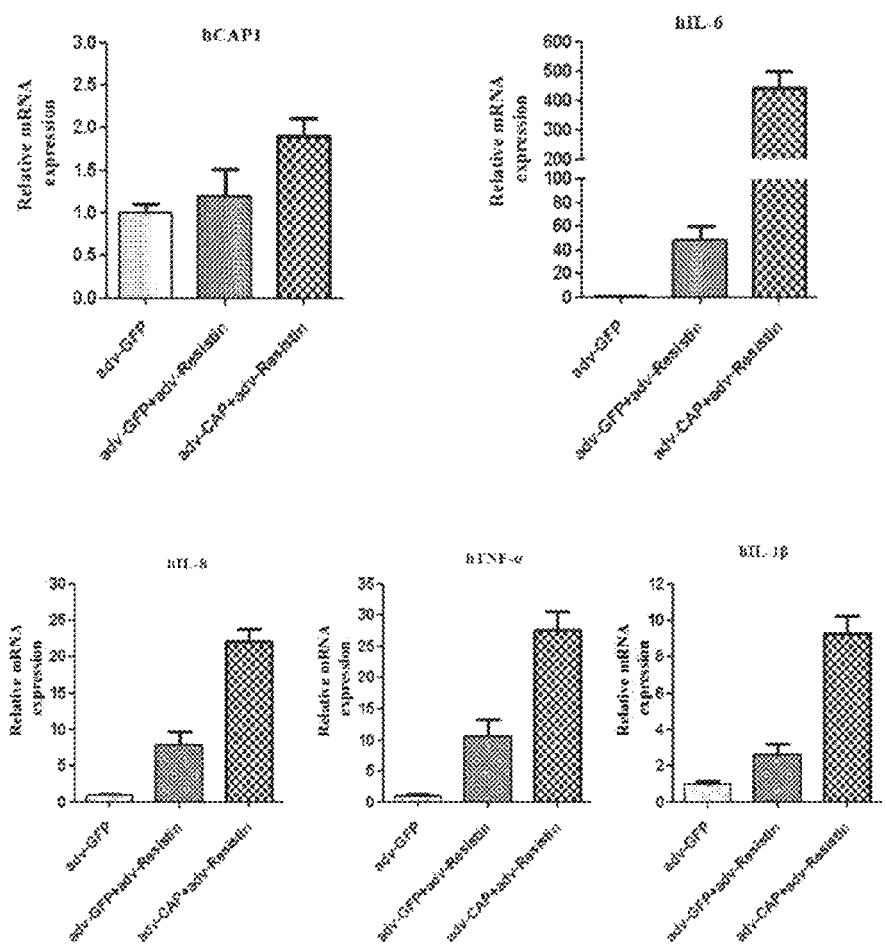
FIG. 32 illustrates an increase of expression of inflammatory cytokines in accordance with an over-expression of CAP1.

According to FIG. 27, it was shown that CAP1 siRNA substantially decreases PKA and NF-kB activity, and according to FIG. 28, it was shown that CAP1 which is a siRNA target decreases expression of cytokine produced against resistin.

9-2. Influence of CAP1 Over-Expression on Transcription of Inflammatory Cytokine After over-expressing human CAP-1 in THP-1 cells by using CAP-1 adenovirus, protein and RNA were extracted, and an effect of CAP-1 over-expression on PKA activity and transcription of inflammatory cytokine was confirmed through western blot and real time PCR, of which results were illustrated in FIG. 29 to FIG. 32.

As shown in FIGS. 29 to 32, resistin has a strong effect in increasing activity of cAMP, PKA, and NF-kB as well as cytokine expression in the cell in which CAP1 is over-expressed.

From the above results, confirmed that CAP1 functioned as a receptor to resistin, and the fact that an interaction between resistin and CAP1 can regulate an increase of cAMP, PKA activity, and NF-kB related to transcription of inflammatory cytokine.

Figure 33:
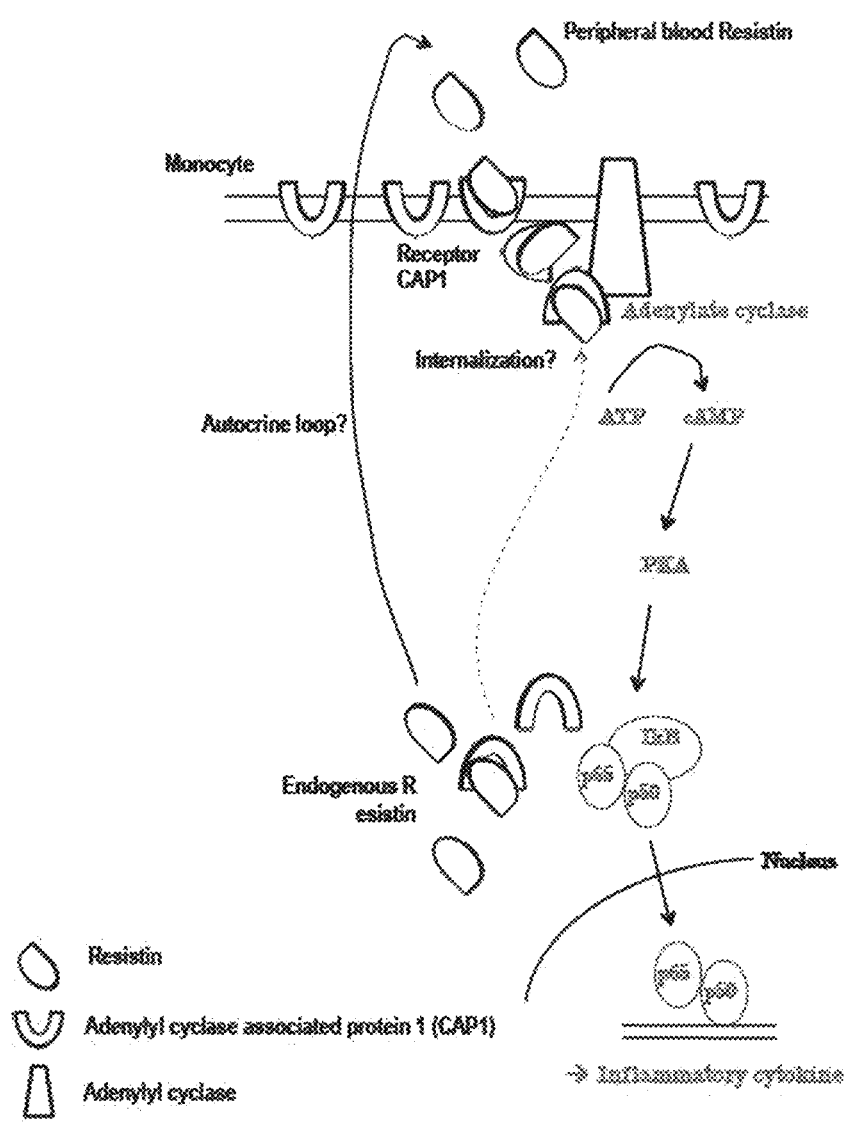
FIG. 33 illustrates a schematic diagram showing a pathway that CAP1 functions as a functional receptor for resistin.

FIG. 33 illustrates a schematic diagram showing how CAP1 protein can behave as a functional receptor for resistin.

Figure 34:
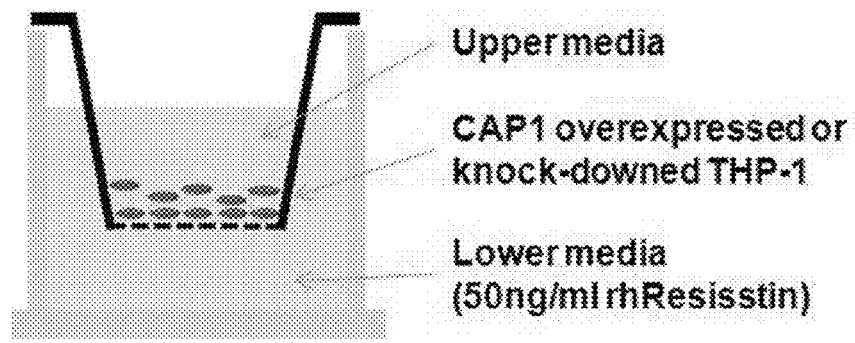
FIG. 34 illustrates a schematic diagram showing a method of transwell migration assay.
Figure 35:
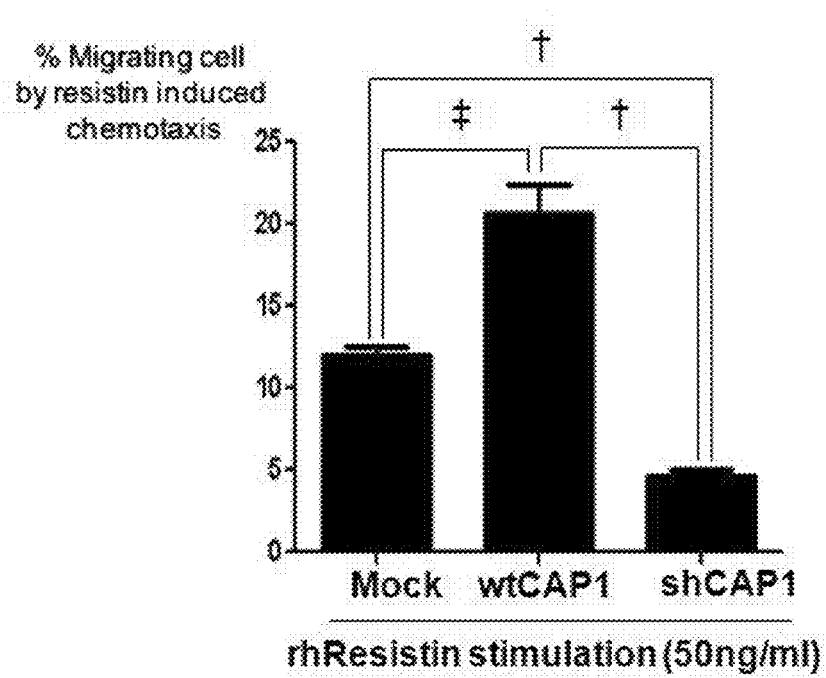
FIG. 35 illustrates a graph of results of transwell migration assay showing a large increase of migration degree towards resistin in the monocyte which over-expresses CAP1 compared with the monocyte in which CAP1 expression is decreased (n=3, *p<0.001, †p<0.01, ‡p<0.05). Scale=500 μm.
Figure 36:
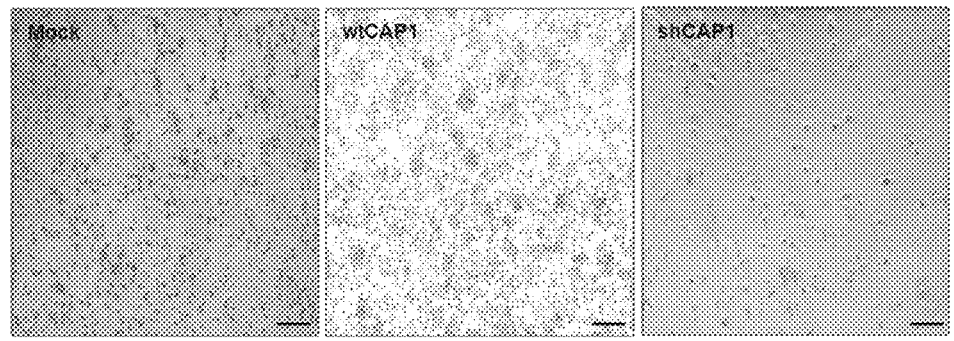
FIG. 36 illustrates results of transwell migration assay showing a large increase of migration degree towards resistin in the monocyte which over-expresses CAP1 compared with the monocyte in which CAP1 expression is decreased.
Figure 37:
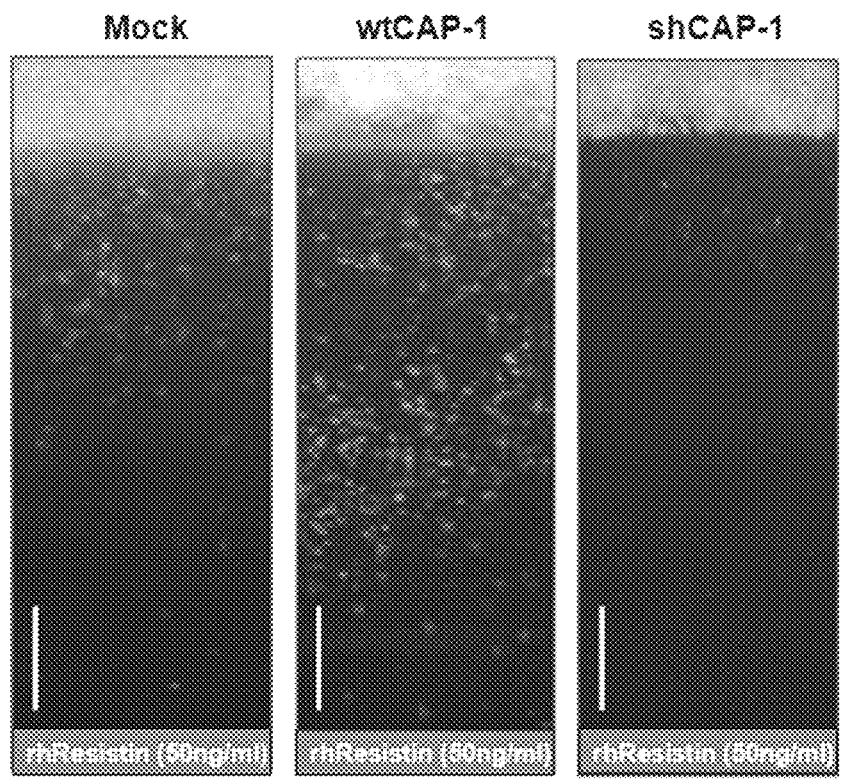
FIG. 37 illustrates results of vertical collagen gel invasion assay showing a large increase of migration degree towards resistin, piercing a collagen layer, in the monocyte which over-expresses CAP1 compared with the monocyte in which CAP1 expression is decreased.
Figure 38:
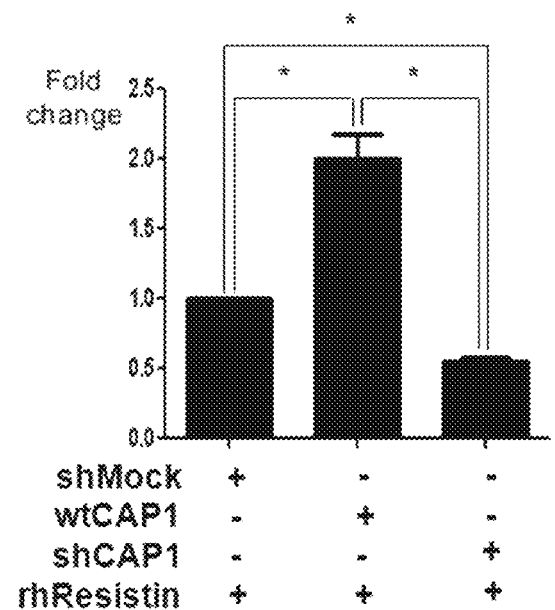
FIG. 38 illustrates a graph of results of vertical collagen gel invasion assay showing a large increase of migration degree towards resistin compared with the monocyte in which CAP1 expression is decreased.

Example 10. Regulation of Inflammation Reaction Mediated by Resistin Through Regulation of CAP1 Expression 10-1. Reaction of Resistin of THP-1 Cell in which CAP1 is Over-Expressed Transwell migration assay (refer to FIG. 34 to FIG. 36) and vertical collagen gel invasion assays (refer to FIG. 37 and FIG. 38) were performed in order to know the reaction towards resistin when CAP1 is over-expressed in human THP-1 cells by using an adenovirus vector.

As shown in FIG. 34 to FIG. 38, a tendency of migration towards resistin was strengthened in THP-1 cells in which CAP1 is over-expressed, whereas a tendency of migration towards resistin was weakened in the cells in which CAP1 expression is decreased. Accordingly, it was shown that the reaction of macrophage or THP-1 cells with resistin is CAP1-dependent.

10-2. Influence of Resistin on Inflammation of White Adipose Tissue when Monocyte in which CAP1 is Over-Expressed and Monocyte in which CAP1 Expression is Decreased are Administered to Mouse When high-fat diet was administered to mouse in which human resistin was over-expressed, instead of expressing murine resistin, in monocyte/macrophage, a larger inflammatory reaction of white adipose tissue was shown. Accordingly, in order to confirm whether an inflammation reaction can be regulated by regulating CAP1 expression in monocyte, the following experiment was performed by using the mouse in which human resistin was expressed, instead of expressing murine resistin.

In particular, a male mouse aged 9 to 10 weeks was used in which human resistin was expressed in monocyte/macrophage and rodents resistin (Retn−/− CD68hR) was not expressed, and CAP1 over-expression was induced by using a lentivirus vector. Inbreeding mice which are Retn−/− were used as control group, and high-fat diet (60% fat, D12492; Uni Faith, Inc.) was administered to all animals for 1 month to induce inflammation of white adipose tissue.

Figure 39:
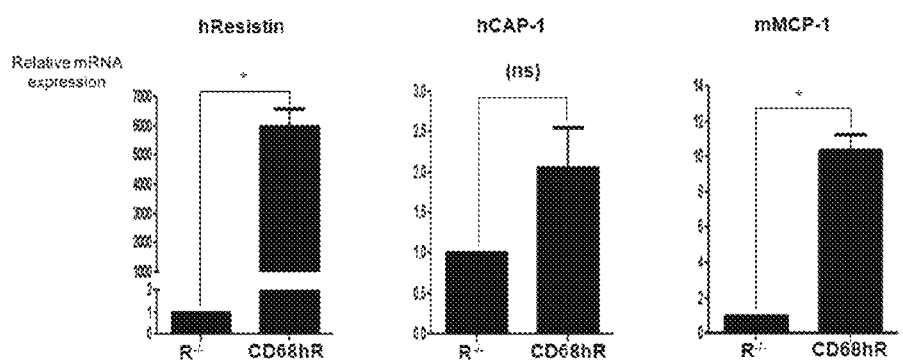
FIG. 39 illustrates a graph showing a high degree of expression of monocyte rhResistin, MCP-1, and CAP-1, higher than the control mouse, when high-fat diet is supplied to CD68hR mouse which expresses human resistin (R−/−; the control mouse in which mouse resistin is knocked out) (n=3, *p<0.001, ns=not significant).

The expression of human resistin and monocyte chemotactic protein-1 (MCP-1) as well as of CAP1 was increased in the mouse to which high fat diet was administered, and the expression of CAP1 showed to be increasing in proportion to the expression of MCP-1 (refer to FIG. 39).

Figure 40:
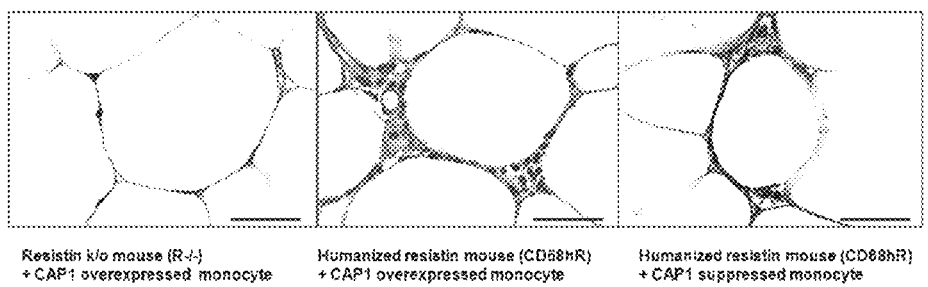
FIG. 40 illustrates a diagram showing infiltration of a large number of macrophages in white adipose tissue when the monocyte which over-expresses CAP1 is systemically introduced in a CD68hR mouse, and infiltration of a less number of macrophages in WAT when the monocyte in which CAP1 expression is decreased (Scale=100 µm).
Figure 41:
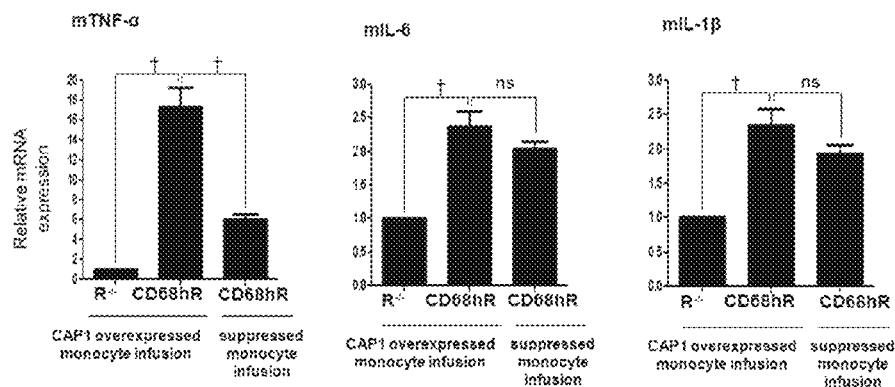
FIG. 41 illustrates a graph showing larger secretion of inflammatory cytokine in white adipose tissue when the monocyte in which CAP1 is over-expressed is introduced, compared with when the monocyte in which CAP1 expression is decreased (n=3, *p<0.001, ‡p<0.05).

As shown in FIG. 40, as a result of administering high-fat diet for 1 month to induce inflammation of white adipose tissue, mouse showed more macrophage pigmentation in white adipose tissue than the control. However, when the monocyte in which CAP1 expression is inhibited was administered to mouse which expresses human resistin, macrophage pigmentation in white adipose tissue (WAT) was greatly decreased. The above results show a tendency consistent with a decrease in expression of inflammation marker, such as TNF-α (refer to FIG. 41). The macrophage infiltrated in WAT was observed with immunofluorescence staining.

Figure 42:
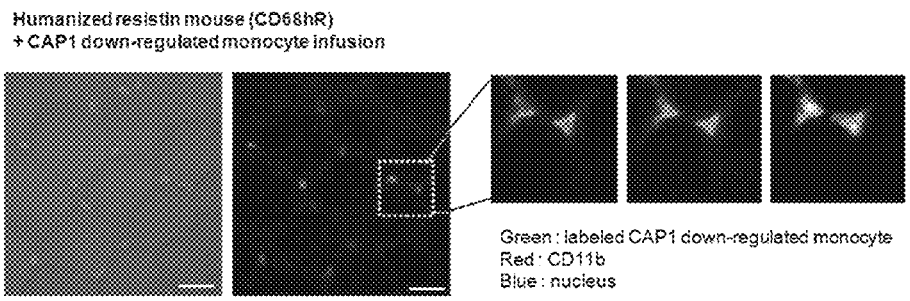
FIG. 42 illustrates an image of immunofluorescence staining showing pigmentation of the monocyte in which CAP1 expression is decreased (Scale=100 µm).
Figure 43:
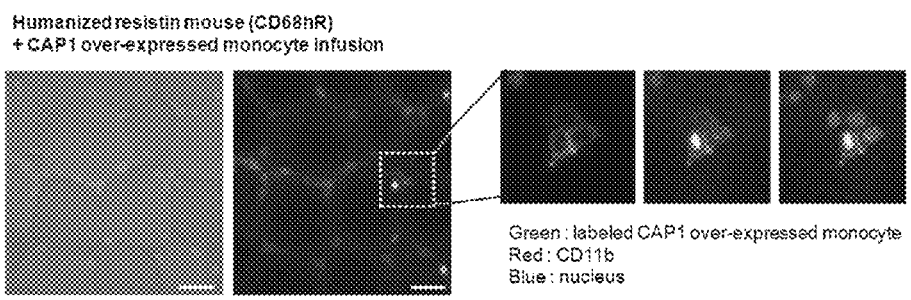
FIG. 43 illustrates an image of immunofluorescence staining showing pigmentation of the monocyte in which CAP1 is over-expressed (Scale=100 µm).
Figure 44:
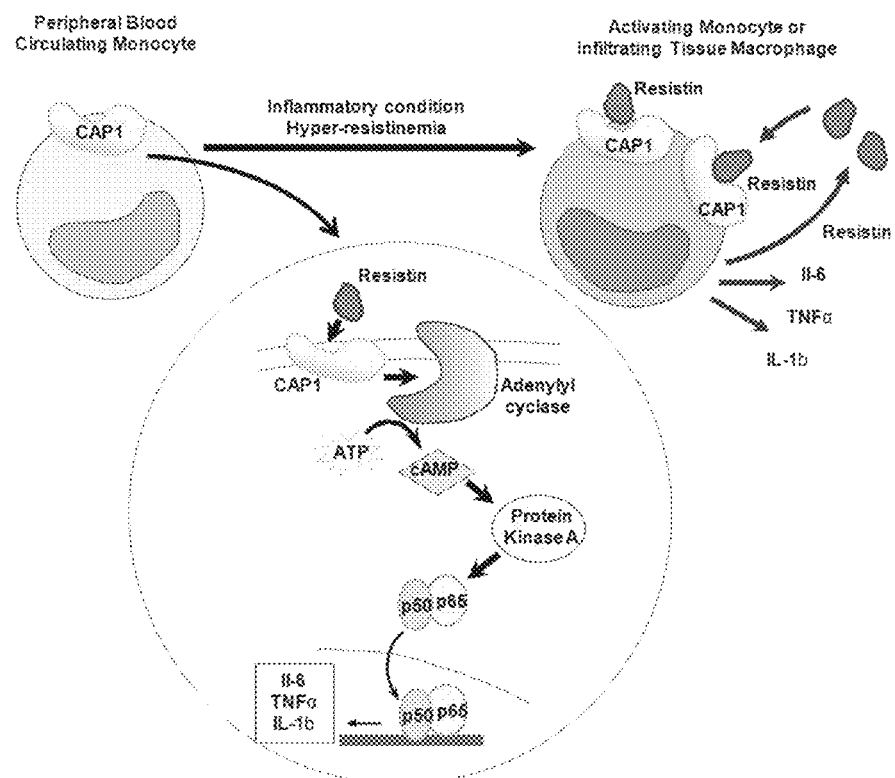
FIG. 44 illustrates a schematic diagram showing that adenylyl cyclase-associated protein 1 (CAP1) functions as a receptor for human resistin.
Figure 45:
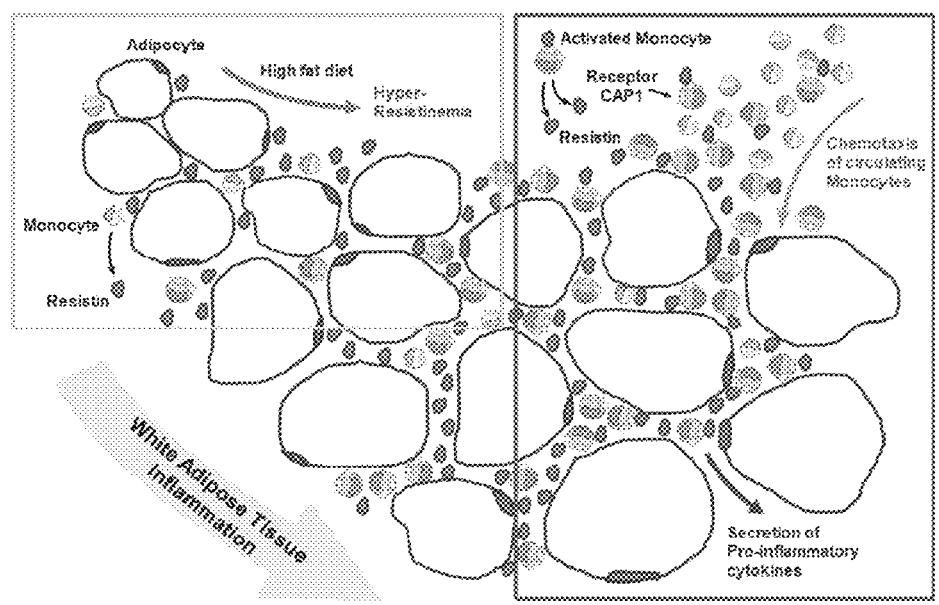
FIG. 45 illustrates a schematic diagram showing that CAP1 mediates induction of biological effect and intracellular signal transduction in the event of adipose tissue inflammation.

As shown in FIG. 42 and FIG. 43, the introduced monocyte (indicates a green color by GFP) migrated towards white adipose tissue which shows inflammation reaction, and thereupon, the monocyte which over-expresses CAP1 (refer to FIG. 43) was much more infiltrated in WAT than the monocyte in which CAP1 expression is decreased (refer to FIG. 42). The monocyte in which CAP1 expression is regulated indicates green color by GFP attached to an expression vector, CD11b is a membrane protein (indicated with red color) which recognizes monocyte, and the cell which recognizes both of them is CAP1 expression regulating monocyte which was introduced from the outside.

From the results, it was shown that CAP1 functions as a receptor for resistin in vivo and at the same time behaves as an important physiological regulator which regulates inflammation reaction of monocyte which is induced by resistin.

The above embodiments of the present invention have been made merely for exemplary purpose, and it will be understood by those skilled in the art that they can be easily modified to other particular forms without departing from the technical idea or necessary characteristics. Therefore, the examples described in the above are merely exemplary and should not be understood to be restrictive.

INDUSTRIAL APPLICABILITY

The present invention can be used in regulation of an inflammatory effect of monocyte, molecular detection of causes for vascular inflammation and arteriosclerosis, and developments of prevention and a treating agent for an inflammatory disease and arteriosclerosis.

The invention claimed is:

1. A method for screening a human resistin protein receptor comprising:
 a) a step of preparing a recombinant vector by cloning mFc-human resistin recombinant DNA to an expression vector, wherein the mFc-human resistin recombinant DNA comprises a nucleic acid encoding an mFc human resistin fusion protein;
 b) a step of expressing the mFc human resistin fusion protein by transfecting the recombinant vector to a cell strain;
 c) a step of forming a complex of the expressed mFc human resistin fusion protein and a human resistin receptor by cultivating the expressed mFc human resistin fusion protein with human acute monocytic leukemia (THP-1) cells;
 d) a step of immuno-precipitating the complex and separating the human resistin receptor from the precipitate; and
 e) a step of confirming the separated human resistin receptor.

2. The method according to claim 1, wherein the expression vector in the step a) is pcDNA3.1.

3. The method according to claim 1, wherein the cell strain in the step b) is a HEK293F cell.

4. The method according to claim 1, further comprising a step of purifying the expressed mFc human resistin fusion protein.

5. The method according to claim 1, wherein the expressed mFc human resistin fusion protein is cultivated together with an anti-mFc-FITC secondary antibody in the step c).

6. The method according to claim 1, wherein beads specific to mFc are used in the immuno-precipitation in the step d).

7. The method according to claim 1, wherein the human resistin receptor in the step d) is a protein having a size of 55 kDa.

8. A method for screening a human resistin protein receptor comprising:
 a) a step of preparing a recombinant vector by cloning mFc-human resistin recombinant DNA to an expression vector, wherein the mFc-human resistin recombinant DNA comprises a nucleic acid encoding an mFc human resistin fusion protein;
 b) a step of expressing mFc human resistin fusion protein by transfecting the recombinant vector to an HEK293F cell;
 c) a step of purifying the expressed mFc human resistin fusion protein;
 d) a step of forming a complex of the expressed mFc human resistin fusion protein and a human resistin receptor by cultivating the purified mFc human resistin fusion protein together with a THP-1 cell;
 e) a step of immuno-precipitating the complex to obtain a precipitate using beads specific to mFc;
 f) a step of separating the human resistin receptor corresponding to a size of 55 kDa from the precipitate; and
 g) a step of confirming the separated human resistin receptor by mass spectrometry.

\* \* \* \* \*

SEQUENCE LISTING

<160> NUMBER OF SEQ ID NOS: 4

<210> SEQ ID NO 1
<211> LENGTH: 92
<212> TYPE: DNA
<213> ORGANISM: Artificial Sequence
<220> FEATURE:
<223> OTHER INFORMATION: forward primer -continued

```
<400> SEQUENCE: 1
cccaagctta tggagacaga cacactcctg ctatgggtac tgctgctctg ggttccaggt    60
tccactggtg acgagcccaa atctagcgac aa                                 92

<210> SEQ ID NO 2
<211> LENGTH: 64
<212> TYPE: DNA
<213> ORGANISM: Artificial Sequence
<220> FEATURE:
<223> OTHER INFORMATION: reverse primer

<400> SEQUENCE: 2
cgagccaccg ccacccgagc caccgccacc cgagccaccg ccacctttac cagggagtgg    60
gaga                                                                64

<210> SEQ ID NO 3
<211> LENGTH: 103
<212> TYPE: PRT
<213> ORGANISM: Saccharomyces cerevisiae

<400> SEQUENCE: 3
```

Glu Leu Ser Gly Leu Pro Ser Gly Pro Ser Ala Gly Ser Gly Pro Pro
1               5                   10                  15

Pro Pro Pro Pro Gly Pro Pro Pro Pro Val Ser Thr Ser Ser Gly
            20                  25                  30

Ser Asp Glu Ser Ala Ser Arg Ser Ala Leu Phe Ala Gln Ile Asn Gln
        35                  40                  45

Gly Glu Ser Ile Thr His Ala Leu Lys His Val Ser Asp Asp Met Lys
    50                  55                  60

Thr His Lys Asn Pro Ala Leu Lys Ala Gln Ser Gly Pro Val Arg Ser
65                  70                  75                  80

Gly Pro Lys Pro Phe Ser Ala Pro Lys Pro Gln Thr Ser Pro Ser Pro
                85                  90                  95

Lys Arg Ala Thr Lys Lys Glu
            100

```
<210> SEQ ID NO 4
<211> LENGTH: 131
<212> TYPE: PRT
<213> ORGANISM: Thermus thermophilus

<400> SEQUENCE: 4
```

Met Glu Val Ser Val Leu Ile Pro Pro Ala Gly Gly Pro Pro Lys
1               5                   10                  15

Ala Phe Leu Gln Val Gly Gly Arg Thr Leu Leu Glu Trp Thr Leu Ala
            20                  25                  30

Ala Phe Arg Asp Ala Ala Glu Val Leu Val Ala Leu Pro Pro Gly Ala
        35                  40                  45

Glu Pro Pro Lys Gly Leu Gly Ala Val Phe Leu Glu Gly Gly Ala Thr
    50                  55                  60

Arg Gln Ala Ser Val Ala Arg Leu Leu Glu Ala Ala Ser Leu Pro Leu
65                  70                  75                  80

Val Leu Val His Asp Val Ala Arg Pro Phe Val Ser Arg Gly Leu Val
                85                  90                  95

Ala Arg Val Leu Glu Ala Ala Gln Arg Ser Gly Ala Ala Val Pro Val
            100                 105                 110

Leu Pro Val Pro Asp Thr Leu Met Ala Pro Glu Gly Glu Ala Tyr Gly

-continued

```
            115                 120                 125
Arg Val Val
    130
```